United States Patent [19]

Debono et al.

[11] Patent Number: 4,820,694

[45] Date of Patent: Apr. 11, 1989

[54] MODIFICATIONS OF 3-O-DEMETHYLMYCINOSE IN MACROCIN AND LACTENOCIN

[75] Inventors: Manuel Debono; Herbert A. Kirst; James P. Leeds, all of Indianapolis, Ind.

[73] Assignee: Eli Lilly and Company, Indianapolis, Ind.

[21] Appl. No.: 912,890

[22] Filed: Sep. 29, 1986

[51] Int. Cl.$^4$ .................. A61K 31/70; C07H 17/08
[52] U.S. Cl. ................................ 514/30; 536/7.1
[58] Field of Search .......................... 536/7.1; 514/30

[56] References Cited

U.S. PATENT DOCUMENTS 4,421,911 12/1983 Fujiwara et al. .................. 536/7.1
4,443,436 4/1984 Kirst et al. ....................... 536/7.1
4,656,258 4/1987 Turner et al. ..................... 536/7.1

FOREIGN PATENT DOCUMENTS 61-143394 7/1986 Japan .

Primary Examiner—Ronald W. Griffin
Assistant Examiner—Elli Peselev
Attorney, Agent, or Firm—Nancy J. Harrison; Leroy Whitaker

[57] ABSTRACT

New 3‴ and/or 4‴-modified macrocin and 3″ and/or 4″-modified-lactenocin derivatives of formula 1 have significant antibacterial activity. Compositions positions containing and methods of using these derivatives are also provided.

36 Claims, No Drawings

MODIFICATIONS OF 3-O-DEMETHYLMYCINOSE IN MACROCIN AND LACTENOCIN

SUMMARY OF THE INVENTION

This invention relates to new macrocin and lactenocin derivatives having formula 1:

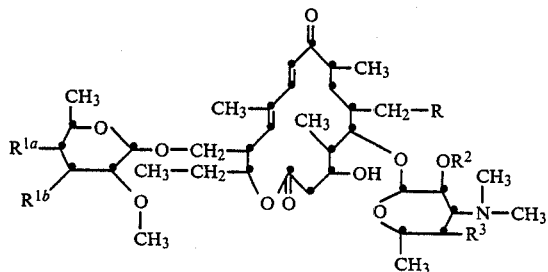

wherein
R is CHO, CH$_2$Z,

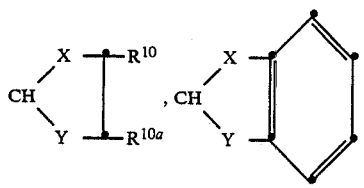

or CH(W)$_2$;
Z is hydrogen, halo, OR$^4$, SR$^5$, N$_3$ or NR$^6$R$^7$;
X and Y independently represent O, S, N-CH$_3$, N-phenyl or N-benzyl;
W is O(C$_1$-C$_4$-alkyl), S-phenyl or S-(R$^{11}$-substituted-phenyl);
R$^{1a}$ and R$^{1b}$ are:
(1) both hydrogen;
(2) independently OH or O(COR$^1$), except that both R$^{1a}$ and R$^{1b}$ cannot be OH unless R$^3$ is hydrogen;
(3) together form a valence bond;
(4) together from a

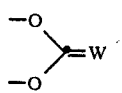

group wherein W represents O or S; or
(5) together form a

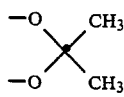

group;
R$^1$ is hydrogen, phenyl R$^{11}$-substituted phenyl, C$_1$-C$_6$-alkyl or C$_1$-C$_6$-alkyl having one to three halo, C$_1$-C$_3$-alkoxy, hydroxy, acetoxy, phenyl, R$^{11}$-substituted-phenyl, pheoxy, R$^{11}$-substituted phenoxy, C$_3$-C$_6$-cycloalkyl, protected-amino or NR$^{12}$R$^{13}$ substituents;
R$^2$ is hydrogen, C$_1$-C$_5$-alkanoyl, halo-substituted-C$_1$-C$_5$-alkanoyl, or benzoyl, phenylacetyl or phenylpropionyl, each of which may have an R$^{11}$ substituent on the phenyl ring;
R$^3$ is hydrogen, OR$^2$ or

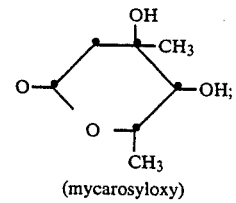

(mycarosyloxy)

R$^4$ is C$_1$-C$_4$-alkyl; C$_1$-C$_4$-alkanoyl; cyclohexyl; phenyl, benzyl, phenethyl or phenoxyethyl, each of which may have an R$^{11}$ substituent on the ring; or a heteroaryl group selected from pyridinyl, pyrimidinyl, pyridazinyl or pyrazinyl;
R$^5$ is C$_1$-C$_4$-alkyl; cyclohexyl; phenyl, benzyl or phenethyl, each of which may have an R$^{11}$ substituent on the phenyl ring; or a heteroaryl group selected from pyridinyl, tetrazolyl, oxazolyl or thiazolyl;
R$^6$ and R$^7$ independently are C$_1$-C$_8$-alkyl or a group of the formula:

(CH$_2$)$_n$(Cyc)

where n is 0, 1 or 2, and Cyc is C$_3$-C$_8$-cycloalkyl, phenyl or R$^{11}$-substituted phenyl; or taken together with the adjacent nitrogen atom form a saturated or unsaturated heterocyclic monocyclic ring containing from 5 to 16 ring atoms or a bicyclic or tricyclic ring system containing from 8 to 20 ring atoms wherein one or more of the ring atoms may be substituted by C$_1$-C$_4$-alkyl, C$_1$-C$_4$-alkoxy, C$_1$-C$_4$-alkoxycarbonyl, hydroxy, C$_1$-C$_4$-alkanoyloxy, halo, NR$^8$R$^9$, phenyl or R$^{11}$-substituted phenyl;
R$^8$ and R$^9$ independently are C$_1$-C$_4$-alkyl or (CH$_2$)$_n$(Cyc); or taken together with the adjacent nitrogen atom form a saturated heterocyclic monocyclic ring containing from 5 to 8 ring atoms;
R$^{10}$ and R$^{10a}$ independently are hydrogen, methyl, phenyl, methoxycarbonyl, ethoxycarbonyl or phenoxycarbonyl; and
R$^{11}$ is halo, C$_1$-C$_3$-alkyl, C$_1$-C$_3$-alkoxy, nitro or hydroxy; and
R$^{12}$ and R$^{13}$ independently are hydrogen, C$_1$-C$_4$-alkyl, (CH$_2$)$_n$(Cyc) or R$^{11}$-substituted-(CH$_2$)$_n$(Cyc) or taken together with the adjacent nitrogen atom form a saturated heterocyclic monocyclic ring containing from 5 to 8 ring atoms or an R$^{11}$-substituted saturated heterocyclic monocyclic ring containing 5 to 8 ring atoms;
and the acid addition salts of these compounds.

The compounds of this invention are useful as antibiotics and/or as intermediates to antibiotics. This invention also relates to pharmaceutical compositions comprising these compounds and to methods of treatment wherein these compounds or compositions are administered to obtain an antibiotic effect or to enhance growth promotion in animals.

DETAILED DESCRIPTION OF THE INVENTION

This invention relates to new antibiotics. In particular, this invention relates to a group of derivatives of the macrolide antibiotics macrocin and lactenocin and to the acid addition salts of these derivatives. This invention also relates to methods of treating certain infections with, methods of promoting growth in animals with, and pharmaceutical compositions comprising the specified derivatives and their pharmaceutically acceptable acid addition salts.

New, improved antibiotics are continually in demand. In addition to antibiotics which are useful for treating human diseases, improved antibiotics are also needed in the veterinary field. Increased potency, expanded spectrum of bacterial inhibition, increased in vivo efficacy, and improved pharmaceutical properties (such as greater oral absorption, higher blood or tissue concentrations, longer body half-life, and more advantageous rate or route or excretion and rate of pattern of metabolism) continue to be goals for improved antibiotics.

Derivatives of macrocin and related macrolides have been made. Unfortunately, many of these derivatives have been either less effective or no better than the parent compounds. One group of superior derivatives was obtained by reductive or protective chemical modification of the C-20 aldehyde group.

We have now discovered another series of derivatives with significant antibiotic activity and oral efficacy. In this series of compounds, the 3'''-and/or 4'''-hydroxyl groups of macrocin or the analogous 3''- and/or 4''-hydroxyl groups of lactenocin have been substituted or together have been removed to give an olefin or deoxy derivative. The novel macrolides of this invention are the compounds shown in formula 1.

Although no stereochemical assignments are indicated in the structures given herein, the stereo-chemistry is identical to that of the antibiotics from which the compounds are prepared, i.e. macrocin and lactenocin.

The term "alkyl" means a hydrocarbon group containing the specified number of carbon atoms. Such groups can be straight, branched or cyclic and can be saturated or unsaturated. The term "cycloalkyl" means a cyclic hydrocarbon group containing the specified number of carbon atoms; such groups can also be saturated or unsaturated. By unsaturated is meant a hydrocarbon group containing double or triple bonds.

The term "alkanoyl" as used herein refers to an acyl moiety derived from a carboxylic acid containing the specified number of carbon atoms. When halo-substituted, the alkanoyl group bears from one to three halo substituents. Acetyl, chloroacetyl, trichloroacetyl, trifluoroacetyl, propionyl, n-butyryl, isobutyryl, n-valeryl and isovaleryl are examples of alkanoyl or halo-substituted alkanoyl groups.

The term "protected-amiino" means that the amino group is substituted by a suitable protecting group. Such a group must be compatible with the other functional groups in the macrolide such that it is readily removed under conditions which leave the rest of the macrolide intact. Appropriate amino-protecting groups are well known (see, for example, T. W. Greene, "Protective Groups in Organic Synthesis," John Wiley and Sons, New York, 1981, Chapter 7). Examples of suitable amino-protecting groups include carbamates such as t-butyl carbamate (BOC group), benzyl carbamate (CBZ group), methyl carbamate and substituted ethyl carbamate such as 2,2,2-trichloroethyl carbamate; amides such as formamide; imides such as phthalimide; N-aralkyl derivatives such as N-benzyl derivatives; and amino acetal derivatives such as N-methoxymethyl derivatives. One especially suitable amino-protecting group is the BOC group.

The term halo refers to a member of the group consisting of Cl, Br, I and F.

When Z is $NR^6R^7$ and the $NR^6R^7$ group is cyclic and unsaturated, representative groups are 1,2,3,6-tetrahydropyridin-1-yl; 1,2,3,4-tetrahydroquinolin-1-yl; 1,2,3,4-tetrahydroisoquinolin-2-yl; indol-1-yl; isoindol-2-yl; indolin-1-yl; isoindolin-2-yl; 2,3,4,5-tetrahydro-1H-1-benzazepin-1-yl; 2,3,4,5-tetrahydro-1H-2-benzazepin-2-yl; 2,3,4,5-tetrahydro-1H-3-benzazepin-3-yl; pyrrol-1-yl; 1H-azepin-1-yl; carbazol-9-yl; 9,10-dihydroacridin-10-yl; and acridin-9-one-10-yl.

When Z is $NR^6R^7$ and the $NR^6R^7$ group is a saturated monocyclic ring, representative groups include pyrrolidin-1-yl, piperidin-1-yl, morpholin-4-yl, thiomorpholin-4-yl, piperazin-1-yl, hexahydroazepin-1-yl, octahydroazocin-1-yl, octahydro-1H-azonin-1-yl, and the like.

When Z is $NR^6R^7$ and the $NR^6R^7$ group is a saturated bicyclic or tricyclic ring, representative groups include decahydroquinolin-1-yl; decahydroisoquinolin-2-yl; decahydrocyclohepta[b]pyrrol-1-yl; decahydrocyclohepta[c]pyrrol-2-yl; decahydrocyclopent[c]azepin-2-yl; decahydrocyclopent[d]azepin-3-yl; an azabicycloheptanyl group such as 3-azabicyclo[3.2.1]-heptan-3-yl; an azabicyclooctanyl group such as 6-azabicyclo[3.2.1]octan-6-yl; an azabicyclononanyl group such as 3-azabicyclo[3.2.2]nonan-3-yl; an azabicyclodecanyl group such as 4-azabicyclo[5.3.1]decan-4-yl; an azatricyclo group such as 2-azatricyclo[6.2.2.2$^{3,6}$]tetradecan-2-yl or dodecahydrocarbazol-9-yl; and a spiro-fused system such as 1-azaspiro[4.5]decan-1-yl.

Representative groups when the $NR^6R^7$ group is a ring wherein one or more of the carbon atoms are substituted include 1,3,3-trimethyl-6-azabicyclo[3.2.1]octan-6-yl; 4-piperidinopiperidin-1-yl; 3,3,5-trimethylhexahydroazepin-1-yl; 4-phenylpiperidin-1-yl; 3,5-dimethylpiperidin-1-yl; N-methylpiperazinyl; and the like.

The formula 1 derivatives are prepared from macrocin and lactenocin via C-20-modified derivatives of these compounds. The structures of the starting antibiotics are shown in formulas 2-5:

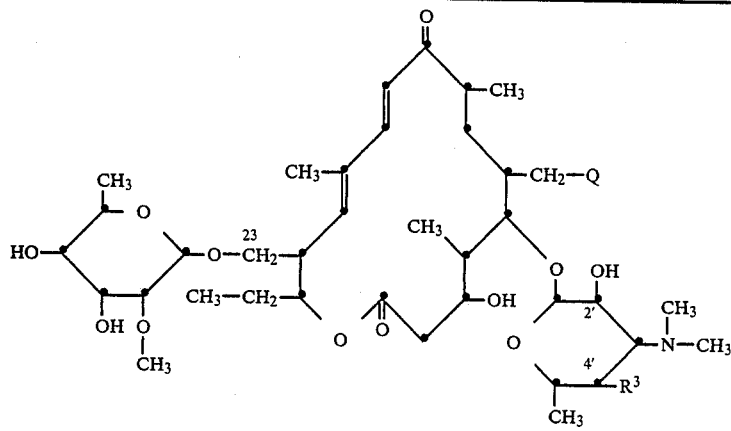

|   | Q   | R³          |
|---|-----|-------------|
| 2 (macrocin): | CHO | O—mycarosyl |
| 3 (lactenocin): | CHO | OH |
| 4 | R | O—mycarosyl |
| 5 | R | OH |

Macrocin and lactenocin are described by Robert L. Hamill et al. in U.S. Pat. No. 3,326,756, issued June 20, 1967. In preparing compounds 4-5, the first step is to modify compounds 2-3 at the C-20 position, using procedures in the art [see, for example, U.S. Pat. Nos. 4,443,436 and 4,440,759; Matsubara et al., Chem. Pharm. Bull 30(1), 97-110 (1982); Omura et al. in J. Antibiotics 37(9), 1007-1015 (1984); and the copending application of Manuel Debono and Herbert A. Kirst, application Ser. No. 517,136, filed July 25, 1983]. The C-20 modified cyclic amino derivatives of the copending application are prepared by two general methods.

Method 1

In this method, the aldehyde group of compound 2 or 3 is first reduced to give the corresponding 20-dihydro compound. The C-20 hydroxyl group in this compound is then converted to a leaving group suitable for displacement reactions by one of two methods. In one method the C-20 hydroxyl group is converted to the trifluoromethanesulfonyloxy (triflate) group, which may be further converted to another leaving group such as iodo, if desired. In the other method, which can be used with lacetenocin, the iodo derivative is directly formed by addition of iodine (which may be dissolved in a suitable solvent such as dimethylformamide) to a solution of the 20-dihydro derivative and triphenylphosphine under nitrogen.

The leaving group at C-20 (iodo, triflate, etc.) is then displaced by reaction with the appropriate amine in a suitable solvent, such as acetonitrile, until formation of the desired 20-modified derivative is complete.

Method 2

In this method, the aldehyde group of compound 2 or 3 is reacted directly with the corresponding amine in the presence of a suitable reducing agent in an appropriate solvent until the desired product is formed. Sodium cyanoborohydride and sodium borohydride are examples of suitable reducing agents, and anhydrous methanol is a useful solvent for this reaction. The reaction may be carried out under a nitrogen atmosphere, but this is usually not required.

As Eddie V. P. Tao and Jeffrey T. Vicenzi describe in U.S. patent application Ser. No. 846,446, filed Mar. 31, 1986, entitled IMPROVED PROCESS FOR PREPARING MACROLIDE DERIVATIVES, formic acid can also be used as the reducing agent.

The C-20-modified derivatives of lactenocin can also be prepared by acidic hydrolysis of mycarose from the corresponding C-20-modified derivatives of macrocin. Procedures of the acidic hydrolysis of mycarose from macrocin to form lactenocin are well known.

The second step (optional) in preparing the C-20-modified derivatives of formula 1, or the first step (optional) in preparing those formula 1 compounds wherein R is formyl, is to protect the hydroxyl groups at the 2'- or 2'- and 4'-positions. The 2'-monoesters of macrocin of the C-20-modified macrocin derivatives and the 2',4'-diesters of lacetenocin or the C-20-modified lactenocin derivatives are prepared by esterifying macrocin, lactenocin or the appropriate C-20-modified derivative on the specified hydroxyl groups by treatment with acylating agents, using standard methods well exemplified in the art (see, for example, U.S. Pat. No. 4,443,436).

The next step in preparing the formula 1 compounds is to esterify the hydroxyl group on the 4-position of the demethylmycinose moiety; this hydroxyl group is at the 4'''-position in macrocin, but is at the 4''-postion in lacetenocin. With the hydroxyl groups at 2' and 4' protected, we have discovered that C-4-hydroxyl group on the demethylmycinose moiety becomes the most reactive hydroxyl group remaining in these highly functionalized molecules. The C-3-hydroxyl group on the demethylmycinose moiety is the next most reactive, and occasionally a minor amount of C-3-monoacyl derivative is obtained with the C-4 monoacyl derivative. Thus, acylation usually gives the C-4 monoacyl derivative and, with the use of more acylating reagent, gives the C-4, C-3-diacyl derivative. A more general route to the C-3-monoacyl derivatives involves blocking the C-4 hydroxyl with an acyl group which is easily removed, such as the trichloroacetyl group, acylating at C-3, and removing the blocking group by standard procedures. The acylating agents and methods of esterification are standard ones which are exemplified in the art and are similar to those described supra.

In the final step, selective removal of the hydroxyl-protecting groups at protected positions, such as at 2' and/or 4' and at 4" or 4'", using standard procedures such as methanolysis, provides the desired formula 1 compound wherein the C-3 and/or C-4 hydroxyl group of the demethylmycinose moiety is acylated (again, see U.s. Pat. No. 4,443,436 for suitable conditions). As recognized in the art, migration of an acyl group from one esterified hydroxyl to a vicinal non-esterified hydroxyl may occur, for instance, during chromatographic purification on supports such as silica gel or by exposure to catalysts such as silica gel.

An alternate approach to the synethsis of (alkylamino)acyl derivatives utilizes 2' and/or 4'-acyl-(3" and/or 4")- or (3'" and/or 4'")-haloacyl derivatives as intermediates. The halo group is then displaced by the alkylamino group to give the 2' and/or 4'-acyl-(3" and/or 4")- or (3'" and/or 4'")-($R^{12}R^{13}N$)-acyl derivatives. Finally, these compounds are selectively deesterified as described supra to give the desired (3" and/or 4")- or (3'" and/or 4'")-($R^{12}R^{13}N$)-acyl derivatives. In each of these steps, standard procedures for displacing the halo group and for selectively de-esterifying are used.

Another approach to the synthesis of (primary or secondary alkylamino)acyl derivatives utilizes the 2' and/or 4'-acyl-(3" and/or 4") or (3'" and/or 4'")-protected-aminoacyl derivatives as intermediates. These compounds are converted to the final products by removal of the amino-protecting groups on the (3" and/or 4") or (3'" and/or 4'") acyl moiety and by selective deesterification as described supra to give the (3Δ and/or 4")- or (3'" and/or 4'")-aminoacyl derivatives. Procedures well recognized in the art for removing amino-protecting groups and for selectively de-esterifying can be used (see, for examplee, U.S. Pat. No. 4,401,660, issued Aug. 30, 1983).

The formula 1 carbonate and thiocarbonate derivatives, i.e., those compounds wherein $R^{1a}$ and $R^{1b}$ together form a

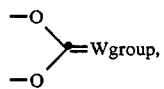=Wgroup, are prepared by treating the corresponding 2' and/or 4'-protected starting materials with a phosgene equivalent, such at 1,1'-carbnyldiimidazole or 1,1'-thiocarbonyldiimidazole, and then deprotecting as described supra, to give the desired compound.

The formula 1 derivatives wherein $R^{1a}$ and $R^{1b}$ together form a valence bond (the olefin derivatives) are prepared from the corresponding thiocarbonate derivatives by an elimination reaction, using reagents such as trivalent phosphorus compounds or low valent transition metal complexes and deprotecting as discussed supra, to give the product. An example of a trivalent phosphorus compound is 1,3-dimethyl-2-phenyl-1,3,2-diazaphospholidine. An example of a low valent transition metal complex is bis(1,5-cyclooctadienyl)nickel.

The formula 1 compounds wherein $R^{1a}$ and $R^{1b}$ are both hydrogen can be prepared from the corresponding olefin compounds by reducing the double bond, using those standard reducing procedures which will selectively reduce the C-3-C4 double bond but will not affect the remaining susceptible positions, to give the desired saturated derivatives.

The ketal derivatives, i.e., the compounds of formula 1 wherein $R^{1a}$ and $R^{1b}$ form a

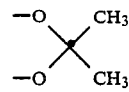

group, can be formed by treating either the corresponding parent or hydroxy-protected compound with acetone or an acetone equivalent and an acid, such as p-toluenesulfonic acid or a Lewis acid, and then removing the protecting group if present. The choice of reaction conditions will determine whether or not mycarose is hydrolyzed or retained on macrocin.

4'-Deoxylactenocin can then be prepared from the 2'-hydroxy-protected-3",4"-ketal derivative of lactenocin, using the procedures outlined in *J. Antibiotics* 34, 1381–1384 (1981), and then deprotecting.

The formula 1 compounds can form acid addition salts. These salts are also useful as antibiotics and are a part of this invention. In another aspect, the salts are useful as intermediates, for example, for separating and purifying the derivatives. In addition, the salts have an improved solubility in water.

Representative suitable salts include those salts formed by standard reactions with both organic and inorganic acids such as, for example, sulfuric, hydrochloric, phosphoric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicyclic, methanesulfonic, benzenesulfonic, sorbic, picric, benzoic, cinnamic, and like acids.

Pharmaceutically acceptable acid addition salts are especially preferred group of salts of this invention.

Illustrative formula 1 compounds are listed in Tables I and II.

TABLE I

Illustrative Formula 1 Derivatives

| Compound No. | R | $R^{1a}$ | $R^{1b}$ | $R^2$ | $R^3$ |
|---|---|---|---|---|---|
| 1 | CHO | acetoxy | OH | acetyl | Myc[a] |
| 2 | " | " | " | H | " |
| 3 | " | " | acetoxy | acetyl | " |
| 4 | " | " | " | H | " |
| 5 | " | isovaleryloxy | OH | acetyl | " |
| 6 | " | " | " | H | " |
| 7 | " | " | isovaleryloxy | acetyl | " |
| 8 | " | " | " | H | " |
| 9 | " | phenylacetoxy | OH | acetyl | " |
| 10 | " | " | " | H | " |
| 11 | " | " | phenylacetoxy | acetyl | " |
| 12 | " | " | " | H | " |
| 13 | " | phenoxyacetoxy | OH | acetyl | " |
| 14 | " | " | " | H | " |
| 15 | " | " | phenoxyacetoxy | acetyl | " |
| 16 | " | " | " | H | " |
| 17 | " | acetoxy | phenylacetoxy | acetyl | " |
| 18 | " | " | " | H | " |
| 19 | " | " | phenoxyacetoxy | acetyl | " |
| 20 | " | " | " | H | " |
| 21 | " | " | OH | acetyl | OH |
| 22 | " | " | " | H | " |
| 23 | " | " | acetoxy | acetyl | " |
| 24 | " | " | " | H | " |
| 25 | " | isovaleryloxy | OH | acetyl | " |
| 26 | " | " | " | H | " |
| 27 | " | " | isovaleryloxy | acetyl | " |
| 28 | " | " | " | H | " |
| 29 | CHO | phenylacetoxy | OH | acetyl | OH |
| 30 | " | " | " | H | " |

TABLE I-continued

Illustrative Formula 1 Derivatives

| Compound No. | R | $R^{1a}$ | $R^{1b}$ | $R^2$ | $R^3$ |
|---|---|---|---|---|---|
| 31 | " | OH | phenylacetoxy | acetyl | " |
| 32 | " | " | " | H | " |
| 33 | " | phenoxyacetoxy | OH | acetyl | " |
| 34 | " | " | " | H | " |
| 35 | " | " | phenoxyacetoxy | acetyl | " |
| 36 | " | " | " | H | " |
| 37 | " | acetoxy | " | acetyl | " |
| 38 | " | " | " | H | " |
| 39 | " | OH | " | " | " |
| 40 | $CH_2OPh$ | acetoxy | acetoxy | acetyl | acetoxy |
| 41 | " | " | " | H | OH |

[a]Myc = Mycarosyloxy

TABLE II

Illustrative Formula 1 Derivatives

| Compound No. | R | $R^{1a}$-$R^{1b}$ Group | $R^2$ | $R^3$ |
|---|---|---|---|---|
| 42 | $CH_2OPh$ | Valance bond | acetyl | acetoxy |
| 43 | $CH_2OPh$ | Valance bond | H | OH |
| 44 | $CH_2$—N (piperidine ring) | Valance bond | acetyl | acetoxy |
| 45 | $CH_2$—N (piperidine ring) | Valance bond | H | OH |
| 46 | $CH_2OPh$ | Valance bond | acetyl | Myc[a] |
| 47 | $CH_2OPh$ | Valance bond | H | Myc[a] |
| 48 | CHO | —O\C(=O)/O— | acetyl | Myc[a] |
| 49 | CHO | —O\C(=O)/O— | H | Myc[a] |
| 50 | CHO | —O\C(=O)/O— | acetyl | acetoxy |
| 51 | CHO | —O\C(=O)/O— | H | OH |
| 52 | $CH_2OPh$ | —O\C(=O)/O— | acetyl | acetoxy |
| 53 | $CH_2OPh$ | —O\C(=O)/O— | H | OH |
| 54 | CHO | —O\C(Me)(Me)/O— | acetyl | acetoxy |
| 55 | CHO | —O\C(Me)(Me)/O— | H | OH |
| 56 | $CH_2OPh$ | —O\C(Me)(Me)/O— | acetyl | acetoxy |
| 57 | $CH_2OPh$ | —O\C(Me)(Me)/O— | H | OH |
| 58 | $CH_2OPh$ | —O\C(=S)/O— | acetyl | acetoxy |
| 59 | $CH_2OPh$ | —O\C(=S)/O— | H | OH |
| 60 | $CH_2OPh$ | —O\C(=S)/O— | acetyl | Myc |
| 61 | $CH_2OPh$ | —O\C(=S)/O— | H | Myc |
| 62 | $CH_2$—N (piperidine) | —O\C(=S)/O— | acetyl | acetoxy |
| 63 | $CH_2$—N (piperidine) | —O\C(=S)/O— | H | OH |

[a]Myc = mycarosyloxy

The derivatives of this invention inhibit the growth of pathogenic bacteria, especially Gram-positive bacteria, Mycoplasma species and Gram-negative bacteria such as Pasteurella species. The derivatives have unexpectedly useful in vivo activity. Particularly unexpected is the ability of these derivatives to treat infections successfully when administered orally.

The minimal inhibitory concentrations (MIC's) at which illustrative compounds inhibit certain bacteria are given in Tables III and IV. The MIC's in Table III were determined by standard agar-dilution assays. The MIC's in Table IV were obtained using conventional brothdilution microtiter tests.

TABLE III

Antibiotic Activity of Formula I Compounds[a]

| Test Organism | Test Compound[b] | | | | | | | | | | | |
|---|---|---|---|---|---|---|---|---|---|---|---|---|
| | 1 | 3 | 5 | 7 | 9 | 10 | 11 | 13 | 15 | 17 | 19 | 21 |
| Staphylococcus aureus X1.1 | 2 | 2 | 2 | 8 | 1 | 1 | 16 | 1 | 4 | 2 | 1 | 2 |
| Staphylpcpccus aureus V41[c] | 2 | 2 | 2 | 8 | 1 | 1 | 16 | 1 | 8 | 2 | 1 | 4 |
| Staphylococcus aureus X400[d] | 4 | 4 | 4 | 16 | 2 | 2 | 64 | 2 | 64 | 4 | 2 | 8 |
| Staphylococcus aureus S13E | 4 | 4 | 2 | 8 | 2 | 1 | 32 | 2 | 32 | 4 | 1 | 4 |
| Staphylococcus epidermidis EPI1 | 2 | 2 | 2 | 8 | 2 | 1 | 32 | 1 | 32 | 4 | 1 | 2 |
| Staphylococcus epidermidis 222 | NT[g] | NT | NT | NT | NT | NT | NT | NT | NT | NT | NT | NT |
| Staphylococcus epidermidis EP12 | 2 | 2 | 2 | 8 | 2 | NT | 32 | 2 | 32 | 2 | 1 | 4 |
| Streptococcus pyogenes C203 | 1 | 1 | 1 | 4 | 0.5 | 0.5 | 4 | 1 | 4 | 1 | 0.5 | 1 |
| Streptococcus pneumoniae Park I | 0.5 | 1 | 0.5 | 2 | 0.25 | 0.25 | 1 | 0.25 | 0.5 | 1 | 0.25 | 1 |
| Streptococcus Group D X66 | 4 | 8 | 2 | 16 | 1 | 1 | 32 | 1 | 32 | 2 | 2 | 4 |
| Streptococcus Group D 2041 | NT | NT | NT | NT | NT | NT | NT | NT | NT | NT | NT | NT |
| Streptococcus Group D 9960 | 4 | 4 | 2 | 8 | 0.5 | 1 | 16 | 1 | 32 | 2 | 2 | 4 |
| Haemophilus influenzae C.L.[e] | 64 | — | — | — | 32 | 32 | — | 64 | — | — | — | NT |
| Haemophilus influenzae 76[f] | 1 | 2 | — | — | 32 | 16 | — | 64 | — | — | — | NT |
| Escherichia coli EC14 | —[h] | — | — | — | — | — | — | — | — | — | — | — |
| Klebsiella pneumoniae X68 | — | — | — | — | — | — | — | — | — | — | — | — |
| Pseudomonas aeruginose X239 | — | — | — | — | — | — | — | — | — | — | — | — |

| Test Organism | 23 | 25 | 26 | 28 | 29 | 30 | 32 | 33 | 34 | 36 | 37 | 38 |
|---|---|---|---|---|---|---|---|---|---|---|---|---|
| Staphylococcus aureus X1.1 | 2 | 2 | 1 | 2 | 1 | 0.5 | 0.5 | 1 | 1 | 2 | 1 | 1 |
| Staphylococcus aureus V41[c] | 2 | 2 | 1 | 2 | 1 | 0.5 | 1 | 1 | 1 | 2 | 1 | 1 |
| Staphylococcus aureus X400[d] | 4 | 2 | 2 | 4 | 1 | 1 | 2 | 2 | 1 | 2 | 2 | 2 |
| Staphylococcus aureus S13E | 2 | 2 | 1 | 2 | 1 | 0.5 | 1 | 1 | 1 | 2 | 1 | 1 |
| Staphylococcus epidermidis EPI1 | 2 | 2 | 1 | 2 | 1 | 0.5 | 0.5 | 1 | 1 | 2 | 1 | 1 |
| Staphylococcus epidermidis 222 | NT | NT | NT | NT | NT | 0.25 | 0.25 | NT | 0.5 | 0.5 | NT | NT |
| Staphylococcus epidermidis EP12 | 2 | NT | NT | NT | 1 | NT | NT | NT | NT | NT | NT | NT |
| Streptococcus pyogenes C203 | 2 | 2 | 0.5 | 2 | 0.5 | 0.25 | 0.25 | 0.5 | 0.12 | 0.5 | 0.5 | 0.5 |
| Streptococcus pneumoniae Park I | 2 | 0.5 | 0.25 | 0.5 | 0.25 | 0.5 | 0.5 | 0.25 | 0.12 | 1 | 0.12 | 0.25 |
| Streptococcus Group D X66 | 8 | 2 | 1 | 4 | 1 | 0.5 | 1 | 1 | 1 | 2 | 1 | 2 |
| Streptococcus Group D 2041 | NT | NT | NT | NT | NT | NT | NT | NT | NT | NT | NT | NT |
| Streptococcus Group D 9960 | 4 | 2 | 1 | 4 | 1 | 1 | 1 | 1 | 1 | 2 | 2 | 2 |
| Haemophilus influenzae C.L.[e] | NT | 32 | 8 | 128 | NT | 8 | 8 | 8 | 4 | 32 | 16 | 16 |
| Haemophilus influenzae 76[f] | NT | 16 | 8 | 64 | NT | 8 | 8 | 8 | 4 | 32 | 4 | 8 |
| Escherichia coli EC14 | — | — | — | — | — | — | — | — | — | — | — | — |
| Klebsiella pneumoniae X68 | — | — | — | — | — | — | — | — | — | — | — | — |
| Pseudomonas aeruginosa X239 | — | — | — | — | — | — | — | — | — | — | — | — |

| Test Organism | 41 | 42 | 43 | 45 | 48 | 49 | 51 | 53 | 55 | 57 | 59 |
|---|---|---|---|---|---|---|---|---|---|---|---|
| Staphylococcus aureus X1.1 | 16 | 1 | 0.25 | 0.12 | 1 | 0.5 | 1 | 1 | 2 | 4 | 1 |
| Staphylococcus aureus V41[c] | 16 | 0.5 | 0.25 | 0.12 | 1 | 0.5 | 2 | 1 | 2 | 4 | 1 |
| Staphylococcus aureus X400[d] | 16 | 0.5 | 0.25 | 0.06 | 2 | 1 | 2 | 1 | 4 | 4 | 1 |
| Staphylococcus aureus S13E | 16 | 4 | 0.25 | 0.06 | 1 | 0.5 | 1 | 1 | 2 | 4 | 1 |
| Staphylococcus epidermidis EPI1 | 16 | 1 | 0.25 | NT | 1 | 1 | 1 | 1 | 2 | 4 | 2 |
| Staphylococcus epidermidis 222 | 8 | 0.5 | 0.12 | 0.12 | 0.5 | 0.25 | 0.5 | 0.5 | 1 | 2 | 0.5 |
| Staphylococcus epidermidis EP12 | NT | NT | NT | NT | NT | NT | NT | NT | NT | NT | NT |
| Streptococcus pyogenes C203 | 16 | 1 | 0.25 | 0.06 | 0.5 | 0.12 | 0.25 | 0.5 | 1 | 2 | 2 |
| Streptococcus pneumoniae Park I | 16 | 1 | 0.5 | 0.06 | 0.12 | 0.12 | 0.25 | 2 | 8 | 8 | 2 |
| Streptococcus Group D X66 | 64 | 4 | 1 | 0.25 | 2 | 1 | 2 | 8 | 32 | 32 | 16 |
| Streptococcus Group D 2041 | 128 | 4 | 1 | 0.5 | 2 | NT | NT | 8 | 16 | 64 | 32 |
| Streptococcus Group D 9960 | NT | NT | NT | NT | NT | 1 | 2 | NT | NT | NT | NT |
| Haemophilus influenzae C.L.[e] | — | — | 32 | 1 | 32 | 32 | 8 | 64 | 16 | — | 128 |
| Haemophilus influenzae 76[f] | — | — | NT | 1 | 16 | 16 | 8 | 32 | 16 | — | 128 |
| Escherichia coli EC14 | — | — | — | 64 | — | — | — | — | — | — | — |
| Klebsiella pneumoniae X68 | — | — | — | 128 | — | — | — | — | — | — | — |
| Pseudomonas aeruginosa X239 | — | — | — | — | — | — | — | — | — | — | — |

[a]MIC in mcg/mL;
[b]Compound numbers from Tables I–II;
[c]Penicillin-resistant strain;
[d]Methicillin-resistant strain;
[e]Ampicillin-sensitive strain;
[f]Ampicillin-resistant strain;
[g]NT = not tested;
[h]Not active at 128 mcg/mL, the highest level tested

TABLE IV

Antibiotic Activity of Formula 1 Compounds[a]

| Test organism | Test Compound[b] | | | | | | | | | | | | | | |
|---|---|---|---|---|---|---|---|---|---|---|---|---|---|---|---|
| | 1 | 3 | 5 | 7 | 9 | 10 | 11 | 13 | 15 | 17 | 19 | 21 | 23 | 25 | 26 |
| Staphylococcus aureus 19C | 6.25 | 6.25 | 3.12 | 12.5 | 3.12 | 1.56 | 50 | 3.12 | 25 | 3.12 | 6.25 | 3.12 | 6.25 | 6.25 | 3.12 |
| Streptococcus sp. 19F | 3.12 | 3.12 | 1.56 | 3.12 | 1.56 | 0.78 | 3.12 | 1.56 | 3.12 | 1.56 | 1.56 | 1.56 | 1.56 | 1.56 | 1.56 |
| Pasteurella multocida 17E[c] | —[e] | — | — | — | — | 50 | — | 50 | — | — | — | 12.5 | 25 | 25 | 25 |
| Pasteurella multocida 60A[d] | — | — | — | — | — | — | — | — | — | — | — | 12.5 | 50 | 25 | 25 |
| Pasteurella multocida 40G | — | — | — | — | — | — | — | — | — | — | — | 12.5 | 50 | 25 | 25 |
| Pasteurella multocida 22A | — | — | — | — | — | — | — | — | — | — | — | 12.5 | 50 | 25 | 25 |
| Pasteurella multocida 68C | — | — | 50 | — | — | 50 | — | 50 | — | — | — | 12.5 | 25 | 25 | 12.5 |
| Pasteurella hemolytica 23C | — | — | — | — | — | — | — | — | — | — | — | 50 | — | 25 | 25 |

TABLE IV-continued

Antibiotic Activity of Formula 1 Compounds[a]

| Test organism | Test Compound[b] | | | | | | | | | | | | | | |
|---|---|---|---|---|---|---|---|---|---|---|---|---|---|---|---|
| Pasteurella hemolytica 41D | — | — | — | — | — | — | — | — | — | — | — | 50 | — | 25 | 50 |
| Pasteurella hemolytica 22C | — | — | — | — | — | — | — | — | — | — | — | 50 | — | 50 | 50 |
| Bordetella bronchiseptica | — | — | — | — | — | — | — | — | — | — | — | 50 | — | 50 | 50 |
| Mycoplasma gallisepticum 29C | 0.78 | 3.12 | 1.56 | 3.12 | 0.78 | 0.39 | 3.12 | 0.39 | 6.25 | 0.39 | 0.78 | 3.12 | 1.56 | 0.39 | 1.56 |
| Mycoplasma gallisepticum 15E | — | — | 50 | 12.5 | 12.5 | 12.5 | 25 | 12.5 | 50 | 12.5 | 25 | 50 | 50 | 50 | 50 |
| Mycoplasma gallisepticum 36H | — | — | 50 | 50 | 12.5 | 12.5 | 50 | 12.5 | 50 | 12.5 | 50 | 50 | 50 | 25 | 50 |
| Mycoplasma synoviae 40A | 1.56 | 12.5 | 1.56 | 3.12 | NT | 1.56 | 12.5 | 0.39 | 3.12 | 1.56 | 0.78 | 3.12 | 6.25 | 3.12 | 3.12 |
| Mycoplasma hyorhinis 29E | 25 | 25 | 1.56 | 6.25 | 1.56 | 3.12 | 12.5 | 3.12 | 6.25 | 3.12 | 3.12 | 6.25 | 12.5 | 1.56 | 1.56 |
| Mycoplasma hyopneumoniae S5972 | NT[f] | NT | NT | NT | NT | NT | NT | NT | NT | NT | NT | NT | NT | NT | NT |
| | 28 | 29 | 30 | 32 | 33 | 34 | 36 | 37 | 38 | 43 | 48 | 49 | 51 | 53 | 55 |
| Staphylococcus aureus 19C | 6.25 | 1.56 | 6.25 | 1.56 | 0.78 | 0.78 | 1.56 | 1.56 | 3.12 | 1.56 | 1.56 | 0.78 | 1.56 | 0.78 | 3.12 |
| Streptococcus sp. 19F | 3.12 | 0.39 | 1.56 | 1.56 | 0.39 | 1.56 | 0.78 | 0.78 | 0.78 | 0.78 | 0.39 | 0.39 | 3.12 | 3.12 | |
| Pasteurella multocida 17E[c] | — | 12.5 | 25 | 25 | 12.5 | 6.25 | 50 | 25 | 25 | 25 | 12.5 | 12.5 | 6.25 | 25 | 25 |
| Pasteurella multocida 60A[d] | — | 25 | 25 | 25 | 6.25 | 12.5 | 50 | 25 | 12.5 | 25 | 25 | 25 | 6.25 | 25 | 50 |
| Pasteurella multocida 40G | 50 | 25 | 25 | 25 | 12.5 | 12.5 | 50 | 25 | 25 | 25 | 25 | 25 | 3.12 | 50 | 25 |
| Pasteurella multocida 22A | — | 25 | 25 | 25 | 12.5 | 12.5 | 50 | 25 | 25 | 50 | 50 | 25 | 6.25 | 50 | 25 |
| Pasteurella multocida 68C | 50 | 6.25 | 12.5 | 12.5 | 6.25 | 12.5 | 25 | 12.5 | 12.5 | 12.5 | 12.5 | 6.25 | 12.5 | 25 | |
| Pasteurella hemolytica 23C | — | 12.5 | 25 | 25 | 12.5 | 25 | 25 | 25 | 25 | 50 | ·50 | 25 | 25 | 50 | 50 |
| Pasteurella hemolytica 41D | — | 12.5 | 50 | 25 | 12.5 | 25 | 25 | 25 | 50 | 50 | 50 | 50 | 12.5 | 50 | 50 |
| Pasteurella hemolytica 22C | — | 12.5 | 50 | 25 | 12.5 | 25 | 50 | 25 | 25 | 50 | — | 50 | 12.5 | 50 | 50 |
| Bordetella bronchiseptica | — | — | — | — | 50 | 50 | — | — | — | — | — | — | — | — | — |
| Mycoplasma gallisepticum 29C | 1.56 | 0.195 | 0.39 | 0.195 | 0.39 | ≦0.048 | 0.39 | 0.195 | 0.39 | 0.39 | 0.195 | 0.195 | 0.39 | 0.195 | 0.39 |
| Mycoplasma gallisepticum 15E | 25 | 12.5 | 12.5 | 12.5 | 12.5 | 25 | 12.5 | 6.25 | 25 | 50 | 12.5 | 25 | 50 | 50 | — |
| Mycoplasma gallisepticum 36H | 50 | 6.25 | 25 | 25 | 12.5 | 12.5 | 12.5 | 12.5 | 12.5 | 25 | 50 | — | — | 50 | — |
| Mycoplasma synoviae 40A | 12.5 | 0.195 | 1.56 | 1.56 | 0.39 | 0.097 | 1.56 | 0.78 | 0.78 | NT | 0.097 | 0.195 | 0.78 | 1.56 | 3.12 |
| Mycoplasma hyorhinis 29E | 6.25 | 1.56 | 1.56 | 1.56 | 3.12 | 6.25 | 6.25 | 6.25 | 12.5 | NT | 1.56 | 0.78 | 3.2 | 25 | 50 |
| Mycoplasma hyopneumoniae S5972 | NT | NT | NT | NT | NT | 0.097 | NT | NT | NT | 6.25 | 0.097 | 0.097 | 0.097 | 3.12 | 0.78 |

[a]MIC in mcg/mL
[b]Compound numbers from Tables I-II
[c]Bovine isolate
[d]Avian isolate
[e]not active at 50 mcg/mL
[f]NT = not tested The formula 1 compounds have shown in vivo antimicrobial activity against experimentally-induced infections in laboratory animals. When two doses of test compound were administered to mice experimentally infected with *S. pyrogenes* C203, the activity observed was measured as an ED$_{50}$ value [effective dose in mg/kg to protect 50% of the test animals: see Warren Wick, et al., *J. Bacteriol.* 81, 233-235 (1961)]. ED$_{50}$ values observed for illustrative compounds are given in Table V.

TABLE V

ED$_{50}$ Values of Formula 1 Compounds vs. *Streptococcus pyogenes* C203 in Mice[a]

| Test Compound[b] | Subcutaneous | Oral |
|---|---|---|
| 59 | 10 | 54 |
| 55 | >10 | >100 |
| 53 | 6.1 | 18.7 |
| 51 | 1.1 | >100 |
| 49 | 1.0 | 85.6 |
| 48 | 1.53 | 28 |
| 43 | >10 | 77.7 |
| 36 | 4.3 | >100 |
| 33 | 1.9 | NT |
| 32 | 4.4 | NT |
| 28 | >6.25 | 21.4 |
| 26 | 5.37 | >25 |
| 23 | 6.8 | NT |
| 21 | 5.5 | NT |
| 17 | >10 | NT |
| 15 | >10 | 87.1 |
| 13 | 7.2 | >100 |
| 10 | 1.9 | 38.8 |
| 7 | >10 | 71.4 |
| 5 | 9.2 | 54.3 |
| 1 | 6.6 | 43.5 |

[a]mg/kg × 2; doses given 1 and 4 hours post-infection
[b]Compound numbers from Tables I-II.

Some of the formula 1 compounds have also shown in vivo antibacterial activity against infections induced by Gram-negative bacteria. Table VI summarizes the results of tests in which illustrative compounds were evaluated against a Pasteurella infection in one-day-old chicks. The compounds were administered by subcutaneous injection at a dosage of 30 mg/kg, 1 and 4 hours post-challenge of the chicks with *Pasteurella multocida* (0.1 ml of a 10$^{-4}$ dilution of a twenty-hour tryptose broth culture of an avian *P. multocida* given subcutaneously). In these tests, unless indicated otherwise, all non-medicated infected chicks died within 24 hours of Pasteurella challenge.

TABLE VI

Activity of Formula 1 Compounds When Administered Subcutaneously to *Pasteurella multocida*-Infected Chicks[a]

| Test Compound[b] | Number of Deaths/Number Treated |
|---|---|
| 9 | 10/10 |
| 21 | 3/10 |
| 23 | 10/10 |
| 29 | 9/10 |
| 33 | 8/10 |

[a]Administered subcutaneously; 30 mg/kg × 2
[b]Compound numbers from TABLE I

This invention also relates to methods of controlling infections caused by bacterial and mycoplasmal species. In carrying out the methods of this invention, an effective amount of a formula 1 compound is administered parenterally or orally to an infected or susceptible warm-blooded animal.

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.1 to about 30 mg/kg. The dose required for oral administration will generally be in the range of from about 1 to about 300 mg/kg and preferably will be in the range of from about 1 to about 100 mg/kg. Suitable dosage regimens can be constructed.

Often the most practical way to administer the compounds is by formulation into the feed supply or drinking water. A variety of feeds, including the common dry feeds, liquid feeds, and pelleted feeds, may be used.

In another aspect, this invention relates to compositions useful for the control of infections caused by bacteria and Mycoplasma species. These compositions comprise a formula 1 compound together with a suitable vehicle. Compositions may be formulated for parenteral or oral administration by methods recognized in the pharmaceutical art.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals or poultry will depend upon the amount of drug to be administered. The common methods of formulating, mixing, and pelleting feeds may be used to prepare feeds containing a formula 1 compound.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alchols, glycols, and carbonate esters such as diethyl carbonate.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable phyisologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrohilicity, density, and surface tension of the liquid suspending medium can assist in making injectable suspensions in individual cases. For example, silicone antifoams, sorbitol, and sugars can be useful suspending agents.

In order to illustrate more fully the operation of this invention, the following examples are provided. In these examples the abbreviation "20-DH" is used for the term "20-dihydro", Ac means acetyl and Ph means phenyl.

Preparation 1

2',4'-Di-O-acetyl-20-DH-20-O-phenyl-lactenocin

A solution of 20-DH-20-O-phenyl-lactenocin (5.0 g, 5.99 mmol, prepared as described in U.S. Pat. No. 4,443,436) and acetic anhydride (1.7 mL, 3 eq.) in acetone (50 mL) was allowed to stand overnight at room temperature. The reaction solution was concentrated in vacuo to a volume of ~20 mL, diluted with a saturated $NaHCO_3$ solution (250 mL), extracted with $CH_2Cl_2$ (4×75 mL), dried ($Na_2SO_4$), and evaporated in dryness to give 5.1 g (92.7%) of the title compound as a white solid foam:

$UV_{max}$ (EtOH): 279 nm ($\epsilon$ 20,771).

IR ($CHCl_3$): 1744, 1714 (sh), 1676, 1592 $cm^{-1}$.

$^1H$ NMR ($CDCl_3$): $\delta$ 4.93 (dd, 2'-H, overlap with 15-H), 4.76 (dd, 4'-H), 2.07 (s, 3H), 2.04 (s, 3H)

MS(FD): m/e 919 (M).

Preparation 2

20-Deoxo-20-(cis-3,5-dimethylpiperidin-1-yl)-lactenocin

A solution of cis-3,5-dimethylpiperidine (8.7 mL, 10 eq.) and lactenocin (5.0 g, 6.61 mmol) in MeOH (100 mL) was treated with $NaBH_3CN$ (415 mg, 3 eq.). The yellow solution was allowed to stand for 1½ hours with the exclusion of moisture, and then was concentrated in vacuo. The residue was diluted with ethyl acetate (100 mL), then extracted with 0.5M pH 5.5 phosphate buffer (2×50 mL) and 0.5M pH 4.5 phosphate buffer (3×50 mL). The pH 4.5 extracts were combined, and the pH was adjusted to pH 8 with 5N NaOH. The basic solution was extracted with ethyl acetate (4×50 mL). The ethyl acetate extracts were dried ($Na_2SO_4$) and evaporated to dryness to give 4.13 g (73.2%) of the title compound.

$UV_{max}$ (EtOH): 283 nm ($\epsilon$ 21,911).

IR ($CHCl_3$): 1735, 1677, 1592 $cm^{-1}$.

$^1H$ NMR ($CDCl_3$): $\delta$ 0.82 (d, 3H, $CH_3$ of piperidine), 0.48 (ddd, axial H of piperidine)

MS(FD): m/e 855 (M+H).

Preparation 3

2',4'-Di-O-acetyl-20-deoxo-20-(cis-3,5-dimethylpiperidin-1-yl)-lactenocin

A solution of 20-deoxo-20-(cis-3,5-dimethylpiperidin-1-yl)-lactenocin (3.06 g, 3.58 mmol) in acetone (40 mL) was treated with acetic anhydride (1.02 mL, 3 eq.). The colorless solution was allowed to stand at room temperature overnight with the exclusion of moisture. The reaction solution was diluted with saturated $NaHCO_3$ solution (500 mL) and extracted with $CH_2Cl_2$ (4×75 mL). The combined $CH_2Cl_2$ extracts were dried ($Na_2SO_4$) and evaporated to dryness. The residue was chromatographed on a silica-gel flash column, using a 1-L gradient of $CH_2Cl_2 \rightarrow CH_2Cl_2/MeOH$ (9:1) followed by 500 mL of $CH_2Cl_2/MeOH$ (9:1) as the eluent, to give 1.96 g (58.3%) of the title compound as a white solid foam.

$UV_{max}$ (EtOH): 283 nm ($\epsilon$ 22,453).

IR ($CHCl_3$): 1743, 1675, 1592 $cm^{-1}$.

$^1H$ NMR ($CHCl_3$): $\delta$ 4.88 (dd, 2'-H, overlap with 15-H), 4.76 (dd, 4'-H), 2.07 (s, 3H), 2.06 (s, 3H).

MS(FD): m/e 939 (M+H).

EXAMPLE 1

2',4',3'',4''-Tetra-O-acetyl-20-DH-20-O-phenyl-lactenocin (Compound 40)

2',4'-Di-O-acetyl-20-DH-20-O-phenyl-lactenocin (1.0 g, 1.09 mmol) was dissolved in $CH_2Cl_2$ (9.0 mL). Acetyl chloride (0.23 mL, 3 eq.) and pyridine (1.0 mL) were added successively by syringe. The solution was allowed to remain at 25° C. for 2 hours with the exclusion of moisture and then was diluted with saturated $NaHCO_3$ solution (50 mL). The mixture was extracted with $CH_2Cl_2$ (4×25 mL), dried ($Na_2SO_4$), and evaporated to dryness. The residue was chromatographed on a Chromatotron (4-mm silica-gel plate), eluting with ethyl acetate, to give 565 mg (51.8%) of the title compound as a white solid foam:

$UV_{max}$ (EtOH): 279 nm ($\epsilon$ 20,144).
IR ($CHCl_3$): 1745, 1678, 1593 $cm^{-1}$.
$^1$H NMR ($CDCl_3$): $\delta$ 5.65 (dd, 3''-H), 4.88 (dd, 2'-H), 4.75 (dd, 4'-H), 4.54 (dd, 4''-H), 2.13 (s, 3H), 2.07 (s, 3H), 2.03 (s, 3H), 2.01 (s, 3H).
MS(FD): m/e 1003 (M).

EXAMPLE 2

3'',4''-Di-O-acetyl-20-DH-20-O-phenyl-lactenocin (Compound 41)

A solution of 3'',4'',2',4'-tetra-O-acetyl-20-DH-20-O-phenyl-lactenocin (500 mg, 0.5 mmol, prepared as described in Example 1) in methanol (15 mL) was heated to 50° C. for 3½ hours. The solution was evaporated to dryness to give the title compound as a white solid foam.

$UV_{max}$ (EtOH): 279 nm ($\epsilon$ 19,910).
IR ($CHCl_3$): 1745, 1680, 1596 $cm^{-1}$.
$^1$H NMR ($CDCl_3$): $\delta$ 5.66 (dd, 3''-H), 4.53 (dd, 4''-H), 2.13 (s, 3H), 2.02 (s, 3H).
MS(FD): m/e 919 (M).

EXAMPLE 3

20-DH-20-O-Phenyl-lactenocin 3'',4''-Carbonate (Compound 53)

A solution of 20-DH-20-O-phenyl-macrocin (1.0 g, 1.02 mmol) in $CH_2Cl_2$ (15 mL) was treated with 1,1'-carbonyldiimidazole (331 mg, 2 eq.). The resulting solution was allowed to stand at room temperature with the exclusion of moisture for 2 hours and then was added to saturated $NaHCO_3$ solution (50 mL). This mixture was extracted with $CH_2Cl_2$ (4×25 mL). The organic layer was dried ($Na_2SO_4$) and evaporated to dryness to give a white solid foam. This residue was treated with 1N $H_2SO_4$ (24 mL) for 1 hour. The solution was then carefully made basic with saturated $NaHCO_3$ solution (125 mL) and extracted with $CH_2Cl_2$ (4×25 mL). The $CH_2Cl_2$ extract was dried ($Na_2SO_4$) and evaporated to dryness. The residue obtained was chromatographed on a Chromatron (4-mm silica-gel plate), eluting with $CH_2Cl_2$/MeOH (9:1, 250 mL, followed by 4:1), to give 338 mg (38.4%) of the title compound as a white solid foam:

$UV_{max}$ (EtOH): 279 nm ($\epsilon$ 20,608).
IR ($CHCl_3$): 1814, 1714, 1677, 1596 $cm^{-1}$.
$^1$H NMR ($CDCl_3$): $\delta$ 4.98 (dd, 3''-H, overlap with 15-H), 4.35 (dd, 4''-H, overlap with 1'-H).
MS(FD): m/e 861 (M).

EXAMPLE 4

20-DH-20-O-Phenyl-lactenocin 3'',4''-thiocarbonate (Compound 59)

A solution of 20-DH-20-O-phenyl-macrocin (5.0 g, 5.1 mmol) in $CH_2Cl_2$ (75 mL) was treated with 1,1'-thiocarbonyldiimidazole (1.8 g, 2 eq.) and allowed to stand at room temperature with the exclusion of moisture for 72 hours. The solution was added to saturated $NaHCO_3$ solution (250 mL), and the mixture was extracted with $CH_2Cl_2$ (3×100 mL). The organic layer was dried ($Na_2SO_4$) and evaporated to dryness to give a yellow-brown solid foam. The foam was treated with 1N $H_2SO_4$ (250 mL) for 16 hours, and then was carefully adjusted to pH 8 with saturated $NaHCO_3$ solution (250 mL) and solid $NaHCO_3$. The mixture was extracted with $CH_2Cl_2$ (4×100 mL), dried ($Na_2SO_4$) and evaporated to dryness. The residue was chromatographed on a silica-gel flash column, eluting with a 1-L gradient of EtOAc/MeOH (4:1→2:1), to give 2.21 g (49.3%) of the title compound as a pale yellow solid foam:

$UV_{max}$ (EtOH): 277 nm ($\epsilon$ 22,000).
IR ($CHCl_3$): 1717, 1679, 1597 $cm^{-1}$.
$^1$H NMR ($CDCl_3$): $\delta$ 5.12 (dd, 3''-H), 4.54 (dd, 4''-H)
MS(FD): m/e 877 (M).

EXAMPLE 5

2',4'-Di-O-acetyl-20-DH-20-O-phenyl-lactenocin 3'',4''-thiocarbonate (Compound 58)

A solution of 2',4'-di-O-acetyl-20-DH-O-phenyl-lactenocin (6.0 g, 6.5 mmol) in $CH_2Cl_2$ (75 mL) was treated with 1,1'-thiocarbonyldiimidazole (2.6 g, 2 eq.) and allowed to stand at room temperature with the exclusion of moisture for 16 hours. The solution was added to saturated $NaHCO_3$ solution (500 mL), and the mixture was extracted with $CH_2Cl_2$ (3×100 mL). The organic layer was dried ($Na_2SO_4$) and evaporated to dryness. The residue was chromatographed on a silica-gel flash column, using ethyl acetate as the eluent, to give 5.2 g (82.9%) of the title compound as a white solid foam:

$UV_{max}$ (EtOH): 278 nm ($\epsilon$ 24,702).
IR ($CHCl_3$): 1745, 1680, 1597 $cm^{-1}$.
$^1$H NMR ($CDCl_3$): $\delta$ 5.14 (dd, 3''-H), 4.92 (dd, 2'-H), 4.75 (dd, 4'H, overlap with 1''), 4.56 (dd, 4''-H), 2.06 (s, 3H), 2.03 (s, 3H)
MS(FD): m/e 961 (M).

EXAMPLE 6

2',4'-Di-O-acetyl-3'',4''-di(dehydrodeoxy)-20-DH-20-O-phenyl-lactenocin (Compound 42)

Method A

2',4'-Di-O-acetyl-20-DH-20-O-phenyl-lactenocin 3'',4''-thiocarbonate (3.0 g, 3.1 mmol) was treated with 1,3-dimethyl-2-phenyl-1,3,2-diazaphospholidine (1.7 mL, 3 eq.) at 40° C. under a flow of dry argon for 5 hours and then was allowed to cool to room temperature overnight. The oil was chromatographed on a silica-gel flash column, eluting with $CH_2Cl_2$/EtOAc (4:1) followed by a gradient of $CH_2Cl_2$/EtOAc (4:1)→EtOAc, to give 395 mg of the title compound as a white solid foam:

$UV_{max}$ (EtOH): 279 nm ($\epsilon$ 25,050).
IR ($CHCl_3$): 1745, 1718 (sh), 1678, 1594 $cm^{-1}$.
$^1$H NMR ($CDCl_3$): $\delta$ 5.71 (dd, 1H), 5.63 (dd, 1H), 4.90 (dd, 2'-H), 4.75 (dd, 4'-H), 2.07 (s, 3H), 2.03 (s, 3H).
MS(FD): m/e 885 (M).

Method B

A mixture of bis-(1,5-cyclooctadiene)nickel (224 mg, 2 eq.) in dry, argon-saturated DMF (5 mL) was frozen in a dry ice/acetone bath. This mixture was treated with a solution of 2',4'-di-OAc-20-DH-20-O-Ph-lactenocin-3'',4''-thiocarbonate (391 mg, 0.4 mmol) in DMF (5 mL), and the resulting solid was allowed to warm slowly to room temperature with the exclusion of air and moisture. After ~16 hours, the dark mixture was heated in an oil bath at 40° C. for 1 hour. The mixture was cooled and then added to saturated NaHCO₃ solution (150 mL). The resulting solution was extracted with $CH_2Cl_2$ (3×50 mL). The $CH_2Cl_2$ solution was dried ($Na_2SO_4$) and concentrated in vacuo. The residue was taken up on $CH_2Cl_2$ (50 mL). The $CH_2Cl_2$ solution was extracted with deionized $H_2O$ (4×50 mL), dried ($Na_2SO_4$) and evaporated in dryness. The residue was chromatographed on a silica-gel flash column, using hexane/ethyl acetate (1:1) as the eluent, to give 201 mg (55.8%) of the title compound as a solid foam.

EXAMPLE 7

3'',4''-Di(dehydrodeoxy)-20-DH-20-O-phenyl-lactenocin (Compound 43)

A solution of 2',4-di-O-acetyl-3'',4''-di(dehydrodeoxy)-20-DH-20-O-phenyl-lactenocin (360 mg, 0.41 mmol) in methanol (10 mL) was allowed to stand at room temperature for 40 hours and then was evaporated to dryness to give the title compound as a colorless glass:

$UV_{max}$ (EtOH): 279 nm ($\epsilon$ 20,947).
IR (CHCl₃): 1713, 1678, 1594 cm⁻¹.
¹H NMR (CDCl₃): δ 5.72 (dd, 1H), 5.65 (dd, 1H).
MS(FD): m/e 801 (M).

EXAMPLES 8–9

2'-O-Acetyl-4'''-O-isovaleryl-macrocin (Compound 5)

2'-O-ACETYL-3''',4'''-di-O-isovaleryl-macrocin (Compound 7)

A solution of 2'-O-acetyl-macrocin (5.0 g, 5.3 mmol) and isovaleryl chloride (1.6 mL, 13.3 mmol) in $CH_2Cl_2$ (150 mL) containing pyridine (1 mL) was stirred for 2 hours at room temperature. Additional isovaleryl chloride (0.64 mL, 5.3 mmol) was then added. The mixture was stirred another hour, and then poured into saturated NaHCO₃ solution. The organic layer was separated, dried ($Na_2SO_4$) and evaporated to dryness to give a yellow oil. This oil was chromatographed on a silica-gel flash column, eluting stepwise with $CH_2Cl_2$ (400 mL) and MeOH/$CH_2Cl_2$ in the following ratios: 1:99 (750 mL) and 2:98; 3:97; 4:96; 6:94 and 8:92 (250 mL each). Fractions were monitored by TLC, using a MeOH/$CH_2Cl_2$/NH₄OH (10:89:1) solvent system. Appropriate fractions were combined to give 2'-O-acetyl-4'''-O-isovaleryl-macrocin (1.634 g, 30% yield) and 2'-O-acetyl-3''',4'''-di-O-isovaleryl-macrocin (1.092 g, 18.5% yield) as white foams.

Compound 5

$UV_{max}$ (MeOH): 281 nm ($\epsilon$ 8,600).
IR (CHCl₃): 1734, 1724, 1675 and 1588.
¹H NMR (CDCl₃): δ 5.0 (dd, 2'-H, overlaps 15), 4.55 (dd, 4'''-H), 2.09 (s, acetyl methyl), ~1.0 (isovaleryl methyls, overlap with 18,17).
MS(FD): m/e 1027 (M).

Compound 7

$UV_{max}$ (MeOH): 282 nm ($\epsilon$ 23,312).
IR (CHCl₃): 1742, ~1730, ~1680 and 1595 cm⁻¹.
¹H NMR (CDCl₃): δ 5.70 (dd, 3'''-H), 5.0 (dd, 2'-H, overlaps 15), 4.55 (dd, 4'''-H, overlaps 1'''-H), 2.09 (s, acetyl methyl), ~1.0 (isovaleryl methyls, overlap with 18 and 17).
MS(FD): m/e 1111 (M).

EXAMPLE 10

2'-O-Acetyl-4''-O-isovaleryl-lactenocin (Compound 25)

2'-O-Acetyl-4'''-O-isovaleryl-macrocin (1.2 g, 1.2 mmol) was dissolved in 1N $H_2SO_4$ (48 mL), and the solution was stirred at room temperature for 1 hour. The reaction mixture was neutralized with a saturated NaHCO₃ solution. The product was extracted with CHCl₃ (2×150 mL). The organic layer was dried ($Na_2SO_4$) and evaporated to dryness to give the title compound as a white foam (842 mg, 79% yield).

$UV_{max}$ (MeOH): 282 nm ($\epsilon$ 22,500).
IR (CHCl₃): 1737, 1724, 1680 and 1593 cm⁻¹.
¹H NMR (CDCl₃): δ 4.98 (dd, 2'-H, overlaps 15), 4.54 (dd, 4''-H), 2.08 (s, acetyl methyl), ~0.98 (isovaleryl methyls, overlap with 18,17).
MS(FD): m/e 883 (M).

EXAMPLE 11

4''-O-Isovaleryl-lactenocin (Compound 26)

2'-O-Acetyl-4''-O-isovaleryl-lactenocin (635 mg, 0.72 mmol) was stirred in MeOH/$H_2O$ (4:1, 38 mL) at 80° for 1 hour. The reaction solution was concentrated in vacuo, diluted with saturated NaHCO₃ solution, and extracted with CHCl₃ (2×150 mL). The organic layer was dried ($Na_2SO_4$) and evaporated to dryness to give the title compound as a white foam (563 mg, 93% yield).

$UV_{max}$ (MeOH): 282 nm ($\epsilon$ 21,750).
IR (CHCl₃): 1723, 1680 and 1592 cm⁻¹.
¹H NMR (CDCl₃): δ 4.54 (dd, 4''-H), ~3.5 (2'-H, overlaps with 5''-H and 2''-methoxy), ~0.98 (isovaleryl methyls, overlap with 18,17).
MS(FD): m/e 842 (M+H).

EXAMPLE 12

2'-O-Acetyl-3'',4''-di-O-isovaleryl-lactenocin (Compound 27)

2-O-Acetyl-3''',4'''-di-O-isovaleryl-macrocin (850 mg, 0.77 mmol) was treated with 1N $H_2SO_4$ (35 mL), using the procedure of Example 10, to give 728 mg (98%) of the title compound.

$UV_{max}$ (MeOH): 282 nm ($\epsilon$ 20,750).
IR (CHCl₃): 1742, 1680 and 1595 cm⁻¹.
MS(FD): m/e 967 (M).

EXAMPLE 13

3'',4''-Di-O-isovaleryl-lactenocin (Compound 28)

2'-O-Acetyl-3'',4''-di-O-isovaleryl-lactenocin (540 mg, 0.56 mmol) was treated with MeOH/$H_2O$ (4:1, 35 mL), using the procedure of Example 11. The product was purified by silica-gel flash chromatography, eluting stepwise with $CH_2Cl_2$ (250 mL) and MeOH/$CH_2Cl_2$ in ratios of 2:98, 4:96, 6:94, 8:92, 1:9, 12:88 and 16:84 (250 mL each), to give the title compound as a white foam (197 mg, 38% yield).

$UV_{max}$ (MeOH): 281 nm ($\epsilon$ 6,700).

IR (CHCl$_3$): 1736, 1675 and 1592 cm$^{-1}$.

$^1$H NMR (CDCl$_3$): δ 5.70 (dd, 3″-H), 4.58 (dd, 4″-H, overlap with 1″-H), ~0.95 (isovaleryl methyls, overlap with 18,17).

MS(FD): m/e 925 (M).

EXAMPLES 14–16

2′-O-Acetyl-4‴-O-phenylacetyl-macrocin (Compound 9)

2′-O-Acetyl-3‴,4‴-di-O-phenylacetylmacrocin (Compound 11)

2′,4‴-Di-O-acetyl-3‴-O-phenylacetylmacrocin (Compound 17)

Using a procedure similar to that of Examples 8–9, 2′-O-acetyl macrocin (2.5 g, 2.7 mmol) was treated with phenylacetyl chloride (1.2 mL, 9 mmol) in CH$_2$Cl$_2$ (75 mL) and pyridine (0.5 mL) and stirred at room temperature for 3 hours. The products were separated by silica-gel flash chromatography eluting stepwise with CH$_2$Cl$_2$ and MeOH/CH$_2$Cl$_2$ as in Examples 8–9. A second silica-gel flash column, again eluting stepwise with MeOH/CH$_2$Cl$_2$ was needed for further purification to give the title compounds as white foams in the following amounts:

2′-O-Acetyl-4‴-O-phenylacetyl-macrocin: (644 mg, 22.5%)

UV$_{max}$ (MeOH): 282 nm (ε 8,800).
IR (CHCl$_3$): 1744, 1724, 1675 and 1588 cm$^{-1}$.
$^1$H NMR (CDCl$_3$): δ 7.30 (m, aromatic), 4.98 (dd, 2′-H, overlaps 15-H), 4.50 (dd, 4‴-H), 3.68 (s, PhAc methylene), 2.06 (s, acetyl methyl).
MS(FD): m/e 1061 (M).

2′-O-Acetyl-3‴,4‴-di-O-phenylacetyl-macrocin: (672 mg, 21.1%)

UV$_{max}$ (MeOH): 281 nm (ε 8,000).
IR (CHCl$_3$): 1743, ~1724, 1675 and 1588 cm$^{-1}$.
$^1$H NMR (CDCl$_3$): δ 7.30 (m, aromatic), 5.70 (dd, 3‴-H), 4.98 (dd, 2′-H, overlaps 15-H), 4.50 (dd, 4‴-H), 3.71, 3.69 (s, s, phenylacetyl methylenes), 2.10 (s, acetyl methyl).
MS(FD): m/e 1179 (M).

2′,4‴-Di-O-acetyl-3‴-O-phenylacetyl-macrocin: (291 mg, 9.8%)

UV$_{max}$ (MeOH): 281 nm (ε 9,000).
IR (CHCl$_3$): 1743, ~1725, 1680 and 1593 cm$^{-1}$.
$^1$H NMR (CDCl$_3$): δ 7.30 (m, aromatic), 5.70 (dd, 3‴-H), 4.98 (dd, 2′-H, overlap with 15), 4.50 (dd, 4‴-H), 3.71 (s, phenylacetyl methylene), 2.15, 2.09 (s, s, acetyl methyls).
MS(FD): m/e 1104 (M+H).

EXAMPLE 17

4‴-O-Phenylacetyl-macrocin (Compound 10)

2′-O-Acetyl-4‴-O-phenylacetyl-macrocin (500 mg, 0.47 mmol) was treated with MeOH/H$_2$O (4:1, 30 mL) as in Example 11 (reaction time=2 hr). The product was purified by silica-gel flash chromatography, eluting stepwise with a MeOH/CH$_2$Cl$_2$ gradient as in Examples 8–9 to give the title compound as a white foam (198 mg, 41% yield).

UV$_{max}$ (MeOH): 282 nm (ε 22,194).
IR (CHCl$_3$): 1723, 1680 and 1595 cm$^{-1}$.
$^1$H NMR (CDCl$_3$): δ 7.32 (m, aromatic), 4.52 (dd, 4‴-H), 3.71 (s, phenylacetyl methylene), 3.55 (dd, 2′-H, overlaps 2‴-OCH$_3$)
MS(FD): m/e 1020 (M+H).

EXAMPLE 18

2′-O-Acetyl-4″-O-phenylacetyl-lactenocin (Compound 29)

2′-O-Acetyl-4‴-O-phenylacetyl-macrocin (400 mg, 0.38 mmol) was treated with 1N H$_2$SO$_4$ (16 mL, 45 minutes reaction time) as in Example 10, to give the title compound as a white foam (305 mg, 87.5%).

UV$_{max}$ (MeOH): 282 nm (ε 18,100).
IR (CHCl$_3$): 1742, 1724, 1675 and 1593 cm$^{-1}$.
$^1$H NMR (CDCl$_3$): δ 7.33 (m, aromatic), 4.98 (dd, 2′-H, overlaps 15), 4.55 (dd, 4″-H), 3.71 (s, phenylacetyl methylene), 2.09 (s, acetyl methyl).
MS(FD): m/e 917 (M).

EXAMPLES 19–20

4″-O-Phenylacetyl-lactenocin (Compound 30)

3″-O-Phenylacetyl-lactenocin (Compound 32)

2′-O-Acetyl-4″-O-phenylacetyl-lactenocin (225 mg, 0.25 mmol) was treated with MeOH/H$_2$O (4:1, 15 mL) at 85° C. as in Example 11. The products were obtained by silica-gel flash chromatography, eluting stepwise with a MeOH/CH$_2$Cl$_2$ gradient as in Examples 8–9, to give the title compounds as white foams in the following amounts.

4″-O-Phenylacetyl-lactenocin: (37 mg, 17%)

UV$_{max}$ (MeOH): 282 nm (ε 21,706).
IR (CHCl$_3$): 1722, 1680 and 1593 cm$^{-1}$.
$^1$H NMR (CDCl$_3$): δ 7.30 (m, aromatic), 4.50 (dd, 4″-H), 4.32 (dd, 3″-H), 3.70 (s, phenylacetyl methylene).
MS(FD): m/e 876 (M+H).

3″-O-Phenylacetyl-lactenocin: (107 mg, 49%)

UV$_{max}$ (MeOH): 282 nm (ε 21,821).
IR (CHCl$_3$): 1722, 1680 and 1593 cm$^{-1}$.
$^1$H NMR (CDCl$_3$): δ 7.30 (m, aromatic), 5.55 (dd, 3″-H), 3.74 (s, phenylacetyl methylene).
MS(FD): m/e 876 (M+H).

EXAMPLES 21–22

2′,4‴-Di-O-acetyl-macrocin (Compound 1)

2′,3‴,4‴-Tri-O-acetyl-macrocin (Compound 3)

Four probe reactions were set up to look at the effect of varying the ratio of acetic anhydride to macrocin. Each contained macrocin (900 mg, 1.0 mmol) in pyridine/CH$_2$Cl$_2$ (1:9, 15 mL) and the following amounts of acetic anhydride: 2 eq. (0.19 mL, 2.0 mmol), 3 eq. (0.28 mL, 3.0 mmol), 4 eq. (0.38 mL, 4.0 mmol) and 5 eq. (0.47 mL, 5.0 mmol). The reactions were carried out for 25 hours. At this time TLC showed that the differences in the reaction products were small, so the four reactions were combined for work-up and purification. The combined reaction mixtures were evaporated under vacuum to remove the volatiles. The residue obtained was dissolved in CH$_2$Cl$_2$ and extracted with saturated NaHCO$_3$ solution. The organic layer was dried (Na$_2$SO$_4$) and evaporated to dryness to give a light yellow foam. This material was chromatographed on a silica-gel flash column as in Examples 8–9, eluting stepwise with a MeOH/CH$_2$Cl$_2$ gradient to give the title compounds as white foams in the following amounts:

2′,4′′′-Di-O-acetyl-macrocin: (1.637 g, 41.5%)

UV$_{max}$ (MeOH): 282 nm ($\epsilon$ 22,205).
IR (CHCl$_3$): 1744, 1723, 1670 and 1593 cm$^{-1}$.
$^1$H NMR (CDCl$_3$): δ 4.98 (dd, 2′-H, overlaps 15-H), 4.52 (dd, 4′′′-H), 4.34 (dd, 3′′′-H), 2.12, 2.06 (s, s, acetyl methyls).
MS(FD): m/e 985 (M).

2′,3′′′,4′′′-Tri-O-acetyl-macrocin: (320 mg, 7.8%),
UV$_{max}$ (MeOH): 282 nm ($\epsilon$ 22,152).
IR (CHCl$_3$): 1746, ~1720, 1670 and 1593 cm$^{-1}$.
$^1$H NMR (CDCl$_3$): δ 4.98 (dd, 2′-H, overlaps 15-H), 5.66 (dd, 3′′′-H), 4.50 (dd, 4′′′-H), 2.16, 2.10, 2.04 (s, s, s, acetyl methyls).
MS(F): m/e 1028 (M+H).

EXAMPLE 23

2′,4′′-Di-O-acetyl-lactenocin (Compound 21)

2′,4′′′-Di-O-acetyl-macrocin (1.0 g, 1.0 mmol) was treated with 1N H$_2$SO$_4$ (40 mL, 55 minutes reaction time) as in Example 10 to give the title compound (604 mg, 71.8%).
UV$_{max}$ (MeOH): 282 nm ($\epsilon$ 21,500).
IR (CHCl$_3$): 1743, 1724, 1670 and 1593 cm$^{-1}$ $^1$H NMR (CDCl$_3$): δ ~5.0 (dd, 2′-H, overlaps 15), 4.55 (dd, 4′′-H), 4.34 (dd, 3′′-H, overlaps 1′), 2.15, 2.09 (s, s, acetyl methyls).
MS(FD): m/e 841 (M).

EXAMPLE 24

2′,3′′,4′′-Tri-O-acetyl-lactenocin (Compound 23)

2′,3′′′,4′′′-Tri-O-acetyl-macrocin (200 mg, 0.2 mmol) was treated with 1N H$_2$SO$_4$ (8 mL, 45 minutes reaction time) as in Example 10 to give the title compound as a white foam (119 mg, 67.4%).
UV$_{max}$ (MeOH): 282 nm ($\epsilon$ 21,000).
IR (CHCl$_3$): 1745, ~1725, 1670 and 1593 cm$^{-1}$.
$^1$H NMR (CDCl$_3$): δ 5.66 (dd, 3′′-H), ~4.98 (dd, 2′-H, overlaps 15), 4.55 (dd, 4′′-H), 2.14, 2.08, 2.02 (s, s, s, acetyl methyls).
MS(FD): m/e 883 (M).

EXAMPLES 25–27

2′-O-Acetyl-4′′′-O-phenoxyacetyl-macrocin (Compound 13)
2′-O-Acetyl-3′′′,4′′′-di-O-phenoxyacetyl-macrocin (Compound 15)
2′,4′′′-Di-O-acetyl-3′′′-O-phenoxyacetyl-macrocin (Compound 19)

2′-O-Acetyl-macrocin (5.0 g, 5.3 mmol) and phenoxyacetyl chloride (2.2 mL, 15.9 mmol) were treated as in Examples 8–9 (1.5-hr reaction time). Two silica-gel flash column runs were needed to obtain the products. The first used a stepwise gradient of toluene/ethyl acetate [4:1 (300 mL), 3:1 (400 mL), 2:1 (300 mL), 3:2 (250 mL), 1:1 (400 mL), 1:2 (600 mL)] to ethyl acetate (400 mL). The second column used a MeOH/CH$_2$Cl$_2$ gradient similar to that in Example 10 to give the title compounds as white foams in the following amounts:

2′-O-Acetyl-4′′′-O-phenoxyacetyl-macrocin: (1.297 g, 22.7%)

UV$_{max}$ (MeOH): 217 nm ($\epsilon$ 4,700) and 278 ($\epsilon$ 7,700),
IR (CHCl$_3$): 1746, 1723, 1680 and 1591 cm$^{-1}$.
$^1$H NMR (CDCl$_3$): δ 7.3, 7.0, 6.94 (m, aromatic), 4.98 (dd, 2′-H, overlaps 15), 4.70 (s, phenoxyacetyl methylene), 4.62 (dd, 4′′′-H, overlaps 1′′′), 2.08 (s, acetyl methyl)
MS(FD): m/e 1077 (M).

2′-O-Acetyl-3′′′,4′′′-di-O-phenoxyacetyl-macrocin: (1.251 g, 19.5%)

UV$_{max}$ (MeOH): 217 nm ($\epsilon$ 15,460) and 276 ($\epsilon$ 23,584).
IR (CHCl$_3$): 1746, ~1725, 1680 and 1591 cm$^{-1}$.
$^1$H NMR (CDCl$_3$): δ 7.3, 7.0, 6.9 (m, aromatic), 5.75 (dd, 3′′′-H), 5.0 (dd, 2′-H, overlaps 15), 4.70 (s, phenoxyacetyl methylene), 4.65 (dd, 4′′′-H), 2.10 (s, acetyl methyl).
MS(FD): m/e 1211 (M).

2′,4′′′-Di-O-acetyl-3′′′-O-phenoxyacetyl-macrocin: (144 mg, 2.4%)

UV$_{max}$ (MeOH): 217 nm ($\epsilon$ 3,600) and 278 ($\epsilon$ 8,000).
IR (CHCl$_3$): 1746, 1724, 1680 and 1592 cm$^{-1}$.
$^1$H NMR (CDCl$_3$): δ 7.3, 7.0, 6.9 (m, aromatic), 5.70 (dd, 3′′′-H), 4.98 (dd, 2′-H, overlaps 15), 4.6 (s, phenoxyacetyl methylene), ~4.65 (dd, 4′′′-H, overlapped), 2.08, 2.10 (s, s, acetyl methyls).
MS(FD): m/e 1119 (M).

EXAMPLE 28

2′-O-Acetyl-4′′-O-phenoxyacetyl-lactenocin (Compound 33)

2′-O-Acetyl-4′′′-O-phenoxyacetyl-macrocin (1.0 g, 0.93 mmol) was treated with 1N H$_2$SO$_4$ (40 mL) as in Example 10 to give the title compound as a white foam (762 mg, 87.8%).
UV$_{max}$ (MeOH): 218 nm ($\epsilon$ 9,750), 280 ($\epsilon$ 22,250).
IR (CHCl$_3$): 1743, 1722, 1680 and 1592 cm$^{-1}$.
$^1$H NMR (CDCl$_3$): δ 7.3, 7.0, 6.9 (m, aromatic), 4.98 (dd, 2′-H, overlaps 15), 470 (s, phenoxyacetyl methylene), ~4.65 (dd, 4′′-H, overlaps 1′′), 2.08 (s, acetyl methyl).
MS(FD): m/e 933 (M).

EXAMPLES 29–30

4′′-O-Phenoxyacetyl-lactenocin (Compound 34)

3′′-O-Phenoxyacetyl-lactenocin (Compound 39)

A mixture of 2′-O-acetyl-4′′-O-phenoxyacetyl-lactenocin and 2′-O-acetyl-3′′-O-phenoxyacetyl-lactenocin (~675 mg, 0.72 mmol) was treated with MeOH/H$_2$O (4:1, 50 mL) at room temperature for 25 minutes as in Example 11. The material obtained was purified by silica-gel flash column chromatography using a MeOH/CH$_2$Cl$_2$ gradient similar to that described in Examples 8–9, to give a mixture of the title compounds (297 mg, 46% yield), of which 80% was compound 34 and 20 % was compound 31.
UV$_{max}$ (MeOH): 217 nm ($\epsilon$ 7,035) and 281 ($\epsilon$ 21,804).
IR (CH$_2$Cl$_2$): 1721, 1680 and 1592 cm$^{-1}$.
$^1$H NMR (CDCl$_3$): 4′′ acylated: δ 7.3, 7.0, 6.9 (m, aromatic), ~4.71 (s, phenoxyacetyl methylene), 4.6 (dd, 4′′-H, overlaps φOAc), 4.35 (dd, 3′′-H (unacylated)); 3′′ acylated: same as 4′′ acylated except δ 5.65 (dd, 3′′-H acylated), ~4.76 (s, phenoxyacetyl methylene at 3′′), 4′′-H unacylated not found.
MS(FD): m/e 891 (M).

EXAMPLE 31

2'-O-Acetyl-3'',4'''-di-O-phenoxyacetyllactenocin (Compound 35)

Using the general procedure of Example 10, 2'-O-acetyl-3''',4'''-di-O-phenoxyacetyl-macrocin (1.0 g, 0.83 mmol) was hydrolyzed (1N $H_2SO_4$, 40 mL) to give the title compound (905 mg crude).

$UV_{max}$ (MeOH): 217 nm ($\epsilon$ 13,500) and 276 ($\epsilon$ 21.750)
IR ($CHCl_3$): 1744, 1680 and 1591 $cm^{-1}$.
MS (FD): m/e 1068 (M+H).

EXAMPLE 32

3'',4''-Di-O-phenoxyacetyl-lactenocin (Compound 36)

2'-O-Acetyl-3'',4''-di-O-phenoxyacetyllactenocin (623 mg, 0.58 mmol) was treated with $MeOH/H_2O$ (4:1, 35 mL) as in Example 11. The material obtained was purified by silica-gel flash column chromatography, using a $MeOH/CH_2Cl_2$ gradient as in Examples 8-9 to give the title compound as a white foam (181 mg, 30% yield).

$UV_{max}$ (MeOH): 217 nm ($\epsilon$ 14,324) and 276 ($\epsilon$ 23,257).
IR ($CHCl_3$): 1770, 1745, 1720, 1680 and 1599 $cm^{-1}$.
$^1H$ NMR ($CDCl_3$): $\delta$ 7.3, 7.0, 6.9 (m, aromatic), 5.77 (dd, 3''-H), 4.7 (s, phenoxyacetyl methylenes), ~4.62 (dd, 4''-H, overlaps phenoxyacetyl methylenes)
MS(FD): m/e 1025 (M).

EXAMPLE 33

2',4''-Di-O-acetyl-3''-O-phenoxyacetyllactenocin (Compound 37)

2',4'''-Di-O-acetyl-3'''-O-phenoxyacetylmacrocin (100 mg, 0.09 mmol) was treated as in Example 10 (5 mL of 1N $H_2SO_4$, 45-min. reaction time) to give the title compound as a white foam (70 mg, 79.8%).

$UV_{max}$ (MeOH): 217 nm ($\epsilon$ 9.326) and 277 ($\epsilon$ 21,123).
$^1H$ NMR ($CDCl_3$): $\delta$ 7.3, 7.0, 6.9 (m, aromatic), 5.7 (dd, 3''-H), 5.0 (dd, 2'-H, overlaps 15), 4.65 (4''-H and phenoxyacetyl methylene), 2.12, 2.09 (s,s, acetyl methyls).
MS(FD): m/e 975 (M).

EXAMPLE 34

4''-O-Acetyl-3''-O-phenoxyacetyl-lactenocin (Compound 38)

2',4''-Di-O-acetyl-3''-O-phenoxyacetyl-lactenocin (50 mg, 0.05 mmol) was treated as in Example 11 [5 mL of $MeOH/H_2O$ (4:1), 30-min. reaction time] to give the title compound as a white foam (39 mg, 83.6% yield).

$UV_{max}$ (MeOH): 218 nm ($\epsilon$ 10,000) and 280 ($\epsilon$ 21,500).
IR ($CHCl_3$): 1741, 1722, 1680 and 1593 $cm^{-1}$.
$^1H$ NMR ($CDCl_3$): $\delta$ 7.3, 7.0, 6.9 (m, aromatic), 5.7 (dd, 3''-H), 4.6 (s, phenoxyacetyl methylene), 4.58 (dd, 4''-H, overlaps phenoxyacetyl methylene), 2.12 (s, acetyl methyl).
MS(FD): m/e 933 (M).

EXAMPLE 35

Macrocin-3''',4''''-Carbonate Derivative (Compound 49)

Macrocin (2.0 g, 2.2 mmol) and 1,1'-carbonyldiimidazole (0.62 g, 3.8 mmol) were dissolved in $CH_2Cl_2$ (25 mL). The reaction mixture was stirred at room temperature for about 3 hours and then worked up and purified by silica-gel flash column chromatography as in Examples 8-9 to give the title compound as a white foam (532 mg, 26% yield).

$UV_{max}$ (MeOH): 281 nm ($\epsilon$ 22,064).
IR ($CHCl_3$): 1815, 1720, 1680 and 1593 $cm^{-1}$.
$^1H$ NMR ($CDCl_3$): $\delta$ 5.0 (3''''-H, overlaps with 1'' and 15), 4.34 (dd, 4'''-H).
MS(FD): m/e 928 (M+H).

EXAMPLE 36

Lactenocin-3'',4''-Carbonate Derivative (Compound 51)

Macrocin-3''',4''''-carbonate derivative (600 mg, 0.65 mmol) was treated with 1N $H_2SO_4$ (25 mL) as in Example 10. The product was purified, using a silica-gel flash column, eluting with a 2-L gradient of hexane:ethyl acetate (1:1) to ethyl acetate and additional ethyl acetate (2.5 L) to give the title compound as a white foam (218 mg, 65%).

$UV_{max}$ (MeOH): 281 nm ($\epsilon$ 21,771).
IR ($CHCl_3$): 1814, 1721, 1680 and 1595 $cm^{-1}$.
$^1H$ NMR ($CDCl_3$): $\delta$ 5.0 (3'''-H, overlaps 15), 4.35 (dd, 4'''-H)
MS(FD): m/e 783 (M).

EXAMPLE 37

3'',4''-Isopropylidene Derivative of Lactenocin (Compound 55)

Macrocin (3.0 g, 2.7 mmol) was dissolved in acetone (50 mL) in the presence of 4A sieves. Four portions of p-toluenesulfonic acid monohydrate were added over ~18 hours (50 mg initially; 150 mg after ~45 minutes; 200 mg after 1.5 hours; 600 mg after ~18 hours: total=1.0 g, 5.3 mmol). After ~22 hours the reaction mixture was filtered and evaporated to dryness. The residue was dissolved in $CH_2Cl_2$ and washed with saturated $NaHCO_3$ solution. The organic layer was dried ($Na_2SO_4$) and evaporated to dryness to give a brown foam. This material was chromatographed on a silica-gel flash column, eluting stepwise with a $MeOH/CH_2Cl_2$ gradient as in Examples 8-9 to give the title compound as a white foam (1.221 g, 56.7%).

$UV_{max}$ (MeOH): 282 nm ($\epsilon$ 21,986).
IR ($CHCl_3$): 1720, 1670 and 1592 $cm^{-1}$.
$^1H$ NMR ($CDCl_3$): $\delta$ 4.53 (dd, 3''-H), ~3.5 (dd, 4''-H), 1.52, 1.40 (s,s, isopropylidene methyls).
MS(FD): m/e 798 (M+H).

EXAMPLE 38

2',4'-Di-O-acetyl-20-deoxo-20-(cis-3,5-dimethylpiperidin-1-yl)-lactenocin-3'',4''-thiocarbonate (Compound 62)

The title compound was prepared by the reaction of 2',4'-di-O-acetyl-20-deoxo-20-(cis-3,5-dimethylpiperidin-1-yl)-lactenocin (1.92 g, 2.05 mmol) with 1,1'-thiocarbonyldiimidazole (729 mg, ~2 eq.) using the procedure described in Example 5. The residue was chromatographed on a Waters Prep 500 LC (silica gel), using ethyl acetate as the eluent, to give 1.40 g (69.8%) of the title compound as a pale yellow solid foam.

$UV_{max}$ (EtOH): 283 nm ($\epsilon$ 22,892) and 236 ($\epsilon$ 17,707).
IR ($CHCl_3$): 1742, 1681, 1596 $cm^{-1}$.
$^1H$ NMR ($CDCl_3$): $\delta$ 5.10 (dd, 3''-H), 4.88 (2'-H, overlap with 15-H), 4.76 (4'-H, overlap with 1''-H), 4.54 (dd, 4''-H).
MS(FD): m/e 981 (M+H).

EXAMPLE 39

2',4'-Di-O-Acetyl-3'',4''-di(dehydrodeoxy)-20-deoxo-20-(cis-3,5-dimethylpiperidin-1-yl)-lactenocin (Compound 44)

2',4'-Di-O-acetyl-20-deoxo-20-(cis-3,5-dimethylpiperidin-1-yl)-lactenocin-3'',4''-thiocarbonate (833 mg, 0.85 mmol) was reacted with bis-(1,5-cyclooctadiene)-nickel (437 mg, 2 eq.) as described in Example 6, Method B. The residue was chromatographed on a silica-gel flash column, using a 1-L gradient of $CH_2Cl_2 \rightarrow CH_2Cl_2/MeOH$ (95:5) followed by 500 mL of $CH_2Cl_2/MeOH$ (95:5) as the eluent, to give 375 mg (48.8%) of the title compound as a white solid foam.

$UV_{max}$ (EtOH): 283 nm ($\epsilon$ 22,360).

IR ($CHCl_3$): 1742, 1678, 1593 $cm^{-1}$.

$^1$H NMR ($CDCl_3$): $\delta$ 5.71 (dd, 1H), 5.64 (dd, 1H).

MS(FD): m/e 905 (M+H).

EXAMPLE 40

3'',4''-Di(dehydrodeoxy)-20-deoxo-20-(cis-3,5-dimethylpiperidin-1-yl)-lactenocin (Compound 45)

A solution of 2',4'-di-O-acetyl-3'',4''-di(dehydrodeoxy)-20-deoxo-20-(cis-3,5-dimethylpiperidin-1-yl)-lactenocin (364 mg, 0.4 mmol) in MeOH (15 mL) was allowed to stand at room temperature for 5 days. The solution was evaporated to dryness to give a colorless glass. The glass was chromatographed on a silica-gel flash column, using a 1-L gradient of $CH_2Cl_2 \rightarrow CH_2Cl/MeOH/conc.$ $NH_4OH$ (90:10:0.5) followed by 750 mL of the latter as the eluent, to give 156 mg (47.2%) of the title compound.

$UV_{max}$ (EtOH): 283 nm ($\epsilon$ 21,091).

IR ($CHCl_3$): 1736, 1676, 1592 $cm^{-1}$.

$^1$H NMR ($CDCl_3$): $\delta$ 5.70 (dd, 1H), 5.64 (dd, 1H).

MS(FD): m/e 821 (M+H).

EXAMPLE 41

20-DH-20-O-Phenyl-lactenocin-3'',4''-isopropylidene Ketal (Compound 57)

A solution of 20-DH-20-O-phenyl-lactenocin (1.0 g, 1.20 mmol) and p-toluenesulfonic acid monohydrate (228 mg, 1.20 mmol) in acetone (15 mL) was allowed to stand over 4 Å sieves at room temperature for 48 hours. The sieves were removed by filtration, and the solution was diluted with saturated $NaHCO_3$ solution (50 mL). The mixture was extracted with $CH_2Cl_2$ (4×25 mL), dried ($Na_2SO_4$) and evaporated to dryness. The residue was chromatographed on a silica-gel flash column, using a 1-L gradient of $CH_2Cl_2/MeOH$ (9:1)$\rightarrow CH_2Cl_2/MeOH$ (4:1) as the eluent, to give 532 mg (50.8%) of the title compound as a solid foam.

$UV_{max}$ (EtOH): 279 nm ($\epsilon$ 21,052).

IR ($CHCl_3$): 1710, 1678; 1594 $cm^{-1}$.

$^1$H NMR ($CDCl_3$): $\delta$ 4.55 (dd, 3''-H), 1.52 (s, 3H), 1.39 (s, 3H).

MS(FD): m/e 875 (M).

We claim:

1. A compound of the formula:

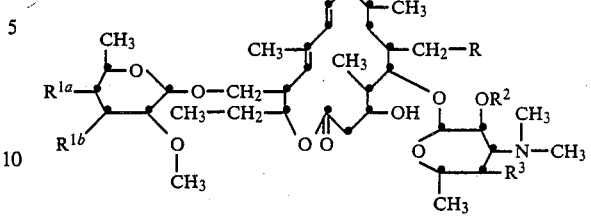

wherein

R is CHO, $CH_2Z$,

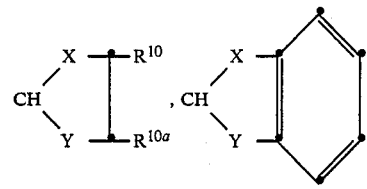

or $CH(W)_2$;

Z is hydrogen, halo, $OR^4$, $SR^5$, $N_3$ or $NR^6R^7$;

X and Y independently represent O, S, N–$CH_3$, N-phenyl or N-benzyl;

W is O($C_1$–$C_4$-alkyl), S-phenyl or S-($R^{11}$-substituted-phenyl);

$R^{1a}$ and $R^{1b}$ are:

(1) both hydrogen;

(2) independently OH or O($COR^1$), except that both $R^{1a}$ and $R^{1b}$ cannot be OH;

(3) together form a valence bond;

(4) together form a

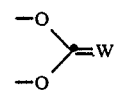

group wherein W represents O or S; or (5) together form a

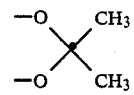

group;

$R^1$ is hydrogen, phenyl, $R^{11}$-substituted phenyl, $C_1$–$C_6$-alkyl or $C_1$–$C_6$-alkyl having one to three halo, $C_1$–$C_3$-alkoxy, hydroxy, acetoxy, phenyl, $R^{11}$-substituted-phenyl, phenoxy, $R^{11}$-substituted phenoxy, $C_3$–$C_6$-cycloalkyl, protected-amino or $NR^{12}R^{13}$ substituents;

$R^2$ is hydrogen, $C_1$–$C_5$-alkanoyl, halo-substituted-$C_1$–$C_5$-alkanoyl, or benzoyl, phenylacetyl or phenylpropionyl, each of which may have an $R^{11}$ substituent on the phenyl ring;

$R^3$ is hydrogen, $OR^2$ or mycarosyloxy;

$R^4$ is $C_1$–$C_4$-alkyl; $C_1$–$C_4$-alkanoyl; cyclohexyl; phenyl, benzyl, phenethyl or phenoxyethyl, each of which may have an $R^{11}$ substituent on the ring; or a heteroaryl group selected from pyridinyl, pyrimidinyl, pyridazinyl or pyrazinyl;

$R^5$ is $C_1$–$C_4$-alkyl; cyclohexyl; phenyl, benzyl or phenethyl, each of which may have an $R^{11}$ substituent on the phenyl ring; or a heteroaryl group selected from pyridinyl, tetrazolyl, oxazolyl or thiazolyl;

$R^6$ and $R^7$ independently are $C_1$–$C_8$-alkyl or a group of the formula:

(CH$_2$)$_n$(Cyc)

where n is 0, 1 or 2, and Cyc is $C_3$–$C_8$-cycloalkyl, phenyl or $R^{11}$-substituted phenyl; or taken together with the adjacent nitrogen atom form a saturated or unsaturated heterocyclic monocyclic ring containing from 5 to 16 ring atoms or a bicyclic or tricyclic ring system containing from 8 to 20 ring atoms wherein one or more of the ring atoms may be substituted by $C_1$–$C_4$-alkyl, $C_1$–$C_4$-alkoxy, $C_1$–$C_4$-alkoxycarbonyl, hydroxy, $C_1$–$C_4$-alkanoyloxy, halo, NR$^8$R$^9$, phenyl or $R^{11}$-substituted phenyl;

$R^8$ and $R^9$ independently are $C_1$–$C_4$-alkyl or (CH$_2$)$_n$(Cyc); or taken together with the adjacent nitrogen atom form a saturated heterocyclic monocyclic ring containing from 5 to 8 ring atoms;

$R^{10}$ and $R^{10a}$ independently are hydrogen, methyl, phenyl, methoxycarbonyl, ethoxycarbonyl or phenoxycarbonyl; and $R^{11}$ is halo, $C_1$–$C_3$-alkyl, $C_1$–$C_3$-alkoxy, nitro or hydroxy; and $R^{12}$ and $R^{13}$ independently are hydrogen, $C_1$–$C_4$-alkyl, (CH$_2$)$_n$(Cyc) or $R^{11}$-substituted-(CH$_2$)$_n$(Cyc) or taken together with the adjacent nitrogen atom form a saturated heterocyclic monocyclic ring containing from 5 to 8 ring atoms or an $R^{11}$-substituted saturated heterocyclic monocyclic ring containing 5 to 8 ring atoms; and the acid addition salts of these compounds.

2. A compound of claim 1 wherein R is CH$_2$Z.
3. A compound of claim 1 wherein R is CHO.
4. A compound of claim 1 wherein R is

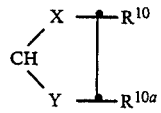

5. A compound of claim 1 wherein R is

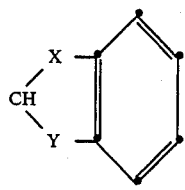

6. A compound of claim 1 wherein R is CH(W)$_2$.
7. A compound of claim 2 wherein Z is OR$^4$.
8. A compound of claim 2 wherein Z is SR$^5$.
9. A compound of claim 2 wherein Z is halo or N$_3$.
10. A compound of claim 2 wherein Z is hydrogen.
11. A compound of claim 2 wherein Z is NR$^6$R$^7$.
12. A compound of claim 7 wherein R$^4$ is $C_1$–$C_4$-alkyl, $C_1$–$C_4$-alkanoyl or cyclohexyl.
13. A compound of claim 7 wherein R$^4$ is phenyl, benzyl, phenethyl or phenoxyethyl, each of which may have an $R^{11}$ substituent on the ring.
14. A compound of claim 13 wherein R$^4$ is phenyl.
15. A compound of claim 7 wherein R$^4$ is a specified heteroaryl group.
16. A compound of claim 11 wherein R$^6$ and R$^7$ independently are $C_1$–$C_8$-alkyl or a group of the formula (CH$_2$)$_n$(Cyc).
17. A compound of claim 16 wherein R$^6$ and R$^7$ are $C_1$–$C_8$-alkyl.
18. A compound of claim 11 wherein R$^6$ and R$^7$ together with the adjacent nitrogen atom form a specified monocyclic ring which may be substituted by $C_1$–$C_4$-alkyl, $C_1$–$C_4$-alkoxy, $C_1$–$C_4$-alkoxycarbonyl, hydroxy, $C_1$–$C_4$-alkanoyloxy, halo, NR$^8$R$^9$, phenyl or $R^{11}$-substituted phenyl.
19. A compound of claim 18 wherein the monocyclic ring is piperidinyl or substituted piperidinyl.
20. A compound of claim 19 wherein the NR$^6$R$^7$ group is 3,5-dimethylpiperidin-1-yl.
21. A compound of claim 11 wherein R$^6$ and R$^7$ together with the adjacent nitrogen atom form a specified bicyclic or tricyclic ring system.
22. A compound of claim 1 wherein R$^{1a}$ and R$^{1b}$ together form a valence bond.
23. A compound of claim 1 wherein R$^{1a}$ and R$^{1b}$ are independently OH or O(COR$^1$).
24. A compound of claim 1 wherein R$^{1a}$ and R$^{1b}$ together form a

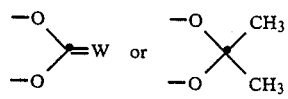

group.

25. A compound of claim 1 wherein R$^{1a}$ and R$^{1b}$ are hydrogen.
26. A compound of claim 1 wherein the salt is pharmaceutically acceptable.
27. A compound of claim 2 wherein the salt is pharmaceutically acceptable.
28. A compound of claim 3 wherein the salt is pharmaceutically acceptable.
29. A composition useful for treating susceptible bacterial infections comprising an effective amount of a compound of claim 26 and a suitable pharmaceutical vehicle.
30. A composition useful for treating susceptible bacterial infections comprising an effective amount of a compound of claim 27 and a suitable pharmaceutical vehicle.
31. A composition useful for treating susceptible bacterial infections comprising an effective amount of a compound of claim 28 and a suitable pharmaceutical vehicle.
32. A composition useful for treating infections caused by susceptible Mycopolasma species comprising an effective amount of a compound of claim 26 and a suitable pharmaceutical vehicle.
33. A method for treating infections caused by susceptible bacteria which comprises administering an effective amount of a composition of claim 29 to an animal.
34. A method for treating infections caused by susceptible bacteria which comprises administering an effective amount of a composition of claim 30 to an animal.

35. A method for treating infections caused by susceptible bacteria which comprises administering an effective amount of a composition of claim 31 to an animal.

36. A method for treating infections caused by susceptible Mycoplasma species which comprises administering an effective amount of a composition of claim 32 to an animal.

* * * * *